US008921656B2

(12) United States Patent
Belknap et al.

(10) Patent No.: US 8,921,656 B2
(45) Date of Patent: Dec. 30, 2014

(54) *SOLANUM BULBOCASTANUM* POLYUBIQUITIN BUL427 PROMOTER AND USES THEREOF

(75) Inventors: William R. Belknap, Albany, CA (US); Sophie S. Chang, Oakland, CA (US); David R. Rockhold, El Cerrito, CA (US); Nathaniel T. Taylor, Hayward, CA (US); Kent F. McCue, El Cerrito, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 1037 days.

(21) Appl. No.: 11/825,500

(22) Filed: Jul. 6, 2007

(65) Prior Publication Data

US 2009/0013422 A1    Jan. 8, 2009

(51) Int. Cl.
*C12N 15/82* (2006.01)
*C12N 15/87* (2006.01)
*C12N 15/63* (2006.01)

(52) U.S. Cl.
CPC ................................. *C12N 15/8216* (2013.01)
USPC ........................ 800/287; 435/320.1; 536/24.1

(58) Field of Classification Search
USPC ....................................................... 800/287
See application file for complete search history.

(56) References Cited

U.S. PATENT DOCUMENTS 6,018,102 A     1/2000  Garbarino et al.
6,787,687 B1 *  9/2004  Giovannoni et al. ...... 800/317.4

OTHER PUBLICATIONS

Kim et al. 1994, Plant Molecular Biology 24: 105-117.*
Oommenn et al 1994, The Plant Cell 6:1789-1803.*
Fourgoux-Nicol et al (1999, Plant Molecular Biology 40 :857-872.*
Garbarino, J.E., Rockhold, D.R., and Belknap, W.R., "Expression of stress-responsive ubiquitin genes in potato tubers," Plant Molecular Biology (1992) 20:235-244.
Garbarino, J.E. and Belknap, W.R., "Isolation of a ubiquitin-ribosomal protein gene (ubi3) from potato and expression of its promoter in transgenic plants" Plant Molecular Biology (1994) 24:119-127.
Garbarino, J.E., Oosumi, T., and Belknap, W.R., "Isolation of a Polyubiquitin Promoter and Its Expression in Transgenic Potato Plants" Plant Phyisol (1995) 109:1371-1378.
Song, J., Dong, F. and Jiang, J., "Construction of a bacterial artificial chromosome (BAC) library for potato molecular cytogenetics research" Genome (2000) 43:199-204.

* cited by examiner

*Primary Examiner* — Li Zheng
(74) *Attorney, Agent, or Firm* — Elizabeth R. Sampson; Lesley Shaw; John Fado

(57) ABSTRACT

The present invention relates to isolated *Solanum Bulbocastanum* Bul427 promoter sequences and uses thereof. An exemplary embodiment provides an isolated plant Bul427 promoter comprising a nucleic acid sequence that is at least about 90% identical to nucleotides 1-1154 of SEQ ID NO:1, wherein the promoter sequence is capable of controlling transcription in a plant. Other exemplary embodiments provide a method for making a transgenic plant, wherein the method comprises transforming a plant, plant part, or plant cell with an expression vector comprising isolated plant Bul427 promoter operably linked to a heterologous nucleic acid sequence, wherein the isolated plant Bul427 promoter is capable of controlling transcription of the heterologous nucleic acid in a plant, and a transgenic plant made by the method and decendants thereof.

17 Claims, 9 Drawing Sheets

```
GCTTGGTCTTACTTCATCGTCGAGAAAAGAAAGAAGACTTCTATCTACAAGTTTAACTCAAACGTAGTTCTTTT
ATTTTTTTGGGTGTGAAGTAGTGTCAAACCAAAATACCCTTTCTAAACAACTATTGTTTGTGAATATAGGTTGT
GTTGTTTCTCATTCGGAAGACCAAGTCCCACACCCTTAAACTTCACTGATGAGAACAACCTCCGCACTCTGGGC
TGTTTAAATCCCCGGTTGAAATCATCCAACCAAACTCTCTTTATTTCGAGATTGAAAAGGTCGATCAATTATGA
TCAAAGATAATGCCTAGTGGCGACGAGCCCACTAGGAAGACCTTTGATTACAAAGGTTACCGTGGTCTAGGTTT
ATAATGGATTCAATTAATCAAAGTGCCTCCAACTCAATCAAAGCTCATTTTCCTATCAGGAGAAAACAATGCAT
AAAAAAGGGATGGCCGTCAAAAAGCCGACCCTTCAATCCAAAAGCGTTCAAATTCCCGCCTACATCAGCTCGAC
CTGTTTGTTCGCTCTAATTAGGATCATCAGAATATCTTGACAGATTTTTTTGAAAAGCTTAACTTGCAAGCGGA
GAATGCCGAGTCTCTACCCACTTTTTGAGCTTGCAAAGTAGCAATATGAAATTTCTTGGGCACTTACCCGTCGT
GCTTGAGATCTAAACTGCTTACAACAACCTTGACCTGGTCCAATGAAAAGAGAAAGACTTAAAGAGCTCCCTCT
ATAGGTGACTCCTCCAATAAGACTCTTAGGGTGCATGTCAAAACCCGCTAAGTTAGGAGTATACATAAAATTTT
GGCCGATATAAGGATTAATATAACCAAATAATATAACGAAAATAAATTTAAACAATAAAAAATAATAAAGAGAT
GTATCCATTCTTTTTCACTCAAATTGTATTTTTAGAAATTATAGTCAAATTTACTATCAAAATTTAAAAAATTA
ATTTTTAAAATTATACATGCCATGAATTTGAAATTTGAAAAAGGGAAAAAGAGGAGAAGCATCTAGTAAGGCTC
TAATTAATTGCGTAACCGTGTCTTCTAAAATATCCGAAGAAATTGCGTAAGCGCTGAGCCATAGGCCCATACGT
TCCCTCTCTGTGACGGCAAAGCGGTTACTATAAATACAGATCTTCCCTTTTTCAACCAAATCCCCAAATCATCA
TCCTTCTCTAGCGCAACTTCTCTCGGAAAAAAGCATCTCCTCCTCCTCTCGTTTTCTCGATAATCTCCTTGTAC
ACTGTTTCTTCTTCTCAAGGTAATGGTCTTTTCTTCTCTCGATTCAATCGTTTGTTGAAGTGATTTAGATTTAT
GCAGGTTTTTGTATTATAAATGTATGAACAGAATTATATGAACGGAATTTACCTTTGTTTCTTGTTTATCGATC
AGATCTGCACGGAATTAGTCGATTTGAGAACTTTTTGAAATCGATGATGTATGTTTTTTCTGTTGATGATGCTA
TAGCGTTTAATTTCGTTTGATTTGCTCTTGTTTTGGTTTCCATATGGTCGAATTGTTGAAGTTTCGTAGTTTGA
TTAGTTTTGTATCCTATCTAGGGTTTTTTGTGATCACAATTAATCAATTTGAAATGGTGATGCTTGCTTTTTCT
GTTGATGATGTTATAGCATTGAATTTCGTTGATTTGCTTGATTTTTTGGTCACTGTTTAATAGAAATTGTTCAA
GTTTCCAGGTTTGATTAATTGTGTCCTGTGTAGGGATATTTATGATCAAATTAATCAATTTGAAGAAAACACT
ATGTTTAATGGATAATATATGCTTTTTTATTTTTCTTGTTGATGATGTTATAGTCTTGTATATTCTCGTGTTGT
TCCATTTTTCTGTTTTCTATTTGCTTGAAATTGTTCAAGTTTCTAGGTTTGATTATTTGTGTGCTATCTAGGGA
TTTTTGTGATCAAAATTACAAATCTAGGTTAAATGGATGATGCATGCTTTTGCTGCTGATGATTTATAGCCTTG
AATTTTGTCGATTTGCTTCATTTTTGGTCTCTATTTAATGAAATTGTTGAAGTTTCTAGGTTTGATTAATTGTG
TCTTGTCTAGGGTTTTTGCGAACAAATTGAACTAGATTTAAATAAATTTAGGAGTCCTCAATTTTTTGTTTGT
TAACTCTTATTGATCTGTTTTTTTAATGTATTTATTCTTGTGTGGGCACATTGTTTATTCTCTTCTGATTATGCT
ACGATCGTGAACTTGATTTACAATACATCCAATTGTGGGTTTGCATCCCTCTTAAAATGATAAGTATAG
TTTGTTCTAGGTAGAATTGGATGCTTCTAGGGGCCTACTGATTTGTTTGTAAAAATGGTTGTTCATTGGATTGA
ATTTTTATTAAAGAAAAAATCTGAAATTCTAATAATTCTTGTAAATTAGGTTGATGTCAGATCTATTTATTTTC
TTCTTTGTTTGGTTGACTGGTCTTCTGGTGGCTCTCTGATTAGTGTAATTATAGTTGACTTTGGATATGTTGCT
TTTGCTCTTTGTATGGTTTCTAATCAATTGGGATTCTTTTCTTATTCTCTCCTAATTTGCCTCTGGTTTGATAT
ATTCAATTTTAACTTCAATTGTTTCGTGGGATGACTTGTCCCAAATTAAACAAGTTCTGAGATTTGTGTGCAAG
CTATGCTATGGGTGTTCATATTATGTGGTAGTTCGCTGCTGTAAGAGGGAGATTGCAGAACCTTTATTATATCG
TCTTTTCTTTTTGGACTTCCAAAGCTTGCTAGTTTGTCATCTCTGCCTGATTGAATAGAATTTTTGACAGTTGT
GTGCTTGAATATATTTCAGATGCAGATCTTTGTTAAGACACTCACCGGAAAGACCATCACTCTTGAGGTCGAGA
GTTCTGACACCATTGATAATGTCAAAGCTAAGATTCAAGACAAGGAAGGCATTCCTCCAGATCAGCAGAGGCTG
ATCTTTGCTGGGAAACAACTTGAAGATGGCCGAACACTTGCTGATTACAACATCCAAAAAGAGTCTACCCTCCA
```

FIG. 1

```
TCTTGTCCTTCGTCTACGTGGTGGAATGCAAATCTTTGTTAAAACTCTGACCGGAAAGACTATAACTCTTGAGG
TCGAGAGTTCAGACACCATTGATAATGTCAAAGCTAAGATTCAAGACAAGGAAGGTATTCCCCCAGACCAGCAG
AGGCTGATCTTTGCTGGGAAACAGCTTGAAGATGGCCGAACACTTGCGGATTACAACATCCAAAAGGAGTCCAC
CCTTCACCTTGTCCTTCGCCTTCGTGGTGGTATGCAGATCTTCGTCAAGACACTTACTGGAAAGACCATCACCC
TTGAAGTTGAAAGTTCAGATACAATTGACAACGTAAAGGCCAAAATTCAGGATAAGGAAGGGATTCCTCCAGAC
CAGCAGAGACTGATCTTTGCCGGCAAGCAACTTGAGGATGGAAGGACCCTGGCTGACTACAATATTCAGAAAGA
GTCTACCTTACATCTTGTTCTTCGTCTGAGGGGTGGCATGCAAATATTTGTTAAGACATTGACAGGGAAGACAA
TTACTTTGGAGGTTGAGAGTTCAGATACTATCGACAATGTTAAAGCAAAGATCCAAGACAAGGAGGGTATTCCT
CCAGACCAGCAGAGATTGATCTTTGCTGGAAAGCAACTTGAGGATGGAAGGACCTTGGCGGATTACAACATTCA
GAAAGAATCAACCCTGCACCTTGTTCTTCGCCTTAGAGGTGGCATGCAAATTTTTGTCAAGACTTTGACGGGGA
AGACAATTACTTTGGAGGTTGAGAGTTCCGATACCATTGACAACGTCAAAGCAAAGATTCAAGACAAGGAGGGT
ATTCCCCCAGACCAGCAGAGATTGATCTTTGCTGGAAAGCAACTTGAAGATGGAAGGACCTTGGCAGATTACAA
CATTCAGAAAGAATCAACCCTGCACCTTGTTCTTCGCCTTAGAGGTGGCATGCAAATTTTTGTCAAGACTTTGA
CTGGGAAGACAATTACATTGGAGGTTGAGAGTTCCGATACCATTGACAACGTCAAAGCAAAGATTCAAGACAAG
GAGGGTATTCCCCCAGACCAGCAGCGTTTGATATTTGCTGGTAAACAACTTGAGGACGGGAGGACTCTTGCAGA
CTATAACATCCAGAAGGAGTCAACTCTCCATTTGGTGTTGCGCTTGAGAGGAGGGATGCAGATCTTTGTGAAGA
CTGACTGGGAAGACAATCACATTGGAGGTGGAGAGCTCTGATACTATTGACAATGTGAAAGCAAAGATACAGGA
CAAGGAAGGGATCCCACCAGATCAACAGAGGCTTATCTTTGCTGGTAAGCAGCTTGAGGATGGTCGCACCCTTG
CAGACTACAATATCCAGAAAGAGTCTACTCTTCATCTTGTCCTCAGGCTCCGTGGCGGGACTTCTGAATGTCC
TGTGTGCTTTGTTGTTTTATTTCCAGACTCAAGTGTTTTTCGTTGTAGTTCTATCTTTCTTTTAAGAGACCTTG
TAATGTGTTATGTTCTGTTGTTTTGTTGCAACCTAAATAAATAAAGATTAGCCGATAAATGTGTTGCATTGTG
AACTTAACACACACTCTCACCCTCCCCCCCTTCTCCCCCCCCCCCCCCCCGCGTCACACGCACACACTCATGA
CTCTGCAGGCACAGGGAAAAGAAGGCATTTTTTACAGTTTGAGAACACCAATAGTTCTTTTTGCAAAAAAACAG
TATTATGGTGGTGGTTTGGTAATACTCTGCTAATAGTGAAGAGTTCTACCCTTGATCTACGCCGTCTTCTTATT
TTGTAACAATTCTTTTATTAAAAGGTGGATGTAAGGACATCATTTTAATCGGTTCACTAAATACTTTCCAACAA
TTTTTTTTTTGTTAAAAAAAGCGCCAGAGGAGAAACTCTCTGCATATCTAGAGGATCTCTAGACTATGGACGAA
AGCTTTGTTTGTGAGGACGGACTCCTGACCATGGGCAACATGAGTCGTGGTTGTCGCAGATCCCCTTTCGCTAT
AGAGGAACCTGTGAGTCTTCTGAATTAGTATTTACAATTCAAATGCTACAACAATGGTTGCTAGTCACTTAGAC
AAAATATAGTTTCATTGTACTACATGTAAATTTGAAGCAAAGTGTTGATATGGACAAATTTCAAAATGGAAACA
GATCCACTCCAGAAGATAAATCCATGTAGTTCTGTCAACTGGTGGCTCTAAGAGGTGGAGAATGATGTAGAAAT
TTGATACATTATGATGAAGTACTCCGCTCTCTATGGGGAAAATTGGGGATACTTGAAACTTAAGTACAAGAAAC
AATAAGTGAAGAAGTTTAGAACTATATGGCACTTAAAAAAGAAGTAGGACTAGGAGGCACTGGAATATCTACTG
TCCCTTTCAGCATCAGTAGAACTTTCTTCTGTGAATGAGGAATCTGGAGATGCCTAACACCAAT
```

FIG. 1 (Cont.)

```
GCTTGGTCTTACTTCATCGTCGAGAAAAGAAAGAAGACTTCTATCTACAAGTTTAACTCAAACGTAGTTCTTTT
ATTTTTTTGGGTGTGAAGTAGTGTCAAACCAAAATACCCTTTCTAAACAACTATTGTTTGTGAATATAGGTTGT
GTTGTTTCTCATTCGGAAGACCAAGTCCCACACCCTTAAACTTCACTGATGAGAACAACCTCCGCACTCTGGGC
TGTTTAAATCCCCGGTTGAAATCATCCAACCAAACTCTCTTTATTTCGAGATTGAAAAGGTCGATCAATTATGA
TCAAAGATAATGCCTAGTGGCGACGAGCCCACTAGGAAGACCTTTGATTACAAAGGTTACCGTGGTCTAGGTTT
ATAATGGATTCAATTAATCAAAGTGCCTCCAACTCAATCAAAGCTCATTTTCCTATCAGGAGAAAACAATGCAT
AAAAAAGGGATGGCCGTCAAAAAGCCGACCCTTCAATCCAAAAGCGTTCAAATTCCCGCCTACATCAGCTCGAC
CTGTTTGTTCGCTCTAATTAGGATCATCAGAATATCTTGACAGATTTTTTTGAAAAGCTTAACTTGCAAGCGGA
GAATGCCGAGTCTCTACCCACTTTTTGAGCTTGCAAAGTAGCAATATGAAATTTCTTGGGCACTTACCCGTCGT
GCTTGAGATCTAAACTGCTTACAACAACCTTGACCTGGTCCAATGAAAAGAGAAAGACTTAAAGAGCTCCCTCT
ATAGGTGACTCCTCCAATAAGACTCTTAGGGTGCATGTCAAAACCCGCTAAGTTAGGAGTATACATAAAATTTT
GGCCGATATAAGGATTAATATAACCAAATAATATAACGAAAATAAATTTAAACAATAAAAAATAATAAAGAGAT
GTATCCATTCTTTTTCACTCAAATTGTATTTTAGAAATTATAGTCAAATTTACTATCAAAATTTAAAAAATTA
ATTTTTAAAATTATACATGCCATGAATTTGAAATTTGAAAAAGGGAAAAAGAGGAGAAGCATCTAGTAAGGCTC
TAATTAATTGCGTAACCGTGTCTTCTAAAATATCCGAAGAAATTGCGTAAGCGCTGAGCCATAGGCCCATACGT
TCCCTCTCTGTGACGGCAAAGCGGTTACTATAAATACAGATCTTCCCTTTTTCAACCAAATCCCCAAATCATCA
TCCTTCTCTAGCGCAACTTCTCTCGGAAAAAAGCATCTCCTCCTCCTCTCGTTTTCTCGATAATCTCCTTGTAC
ACTGTTTCTTCTTCTCAAGGTAATGGTCTTTTCTTCTCGATTCAATCGTTTGTTGAAGTGATTTAGATTTAT
GCAGGTTTTTGTATTATAAATGTATGAACAGAATTATATGAACGGAATTTACCTTTGTTTCTTGTTTATCGATC
AGATCTGCACGGAATTAGTCGATTTGAGAACTTTTTGAAATCGATGATGTATGTTTTTCTGTTGATGATGCTA
TAGCGTTTAATTTCGTTTGATTTGCTCTTGTTTTGGTTTCCATATGGTCGAATTGTTGAAGTTTCGTAGTTTGA
TTAGTTTTGTATCCTATCTAGGGTTTTTTGTGATCACAATTAATCAATTTGAAATGGTGATGCTTGCTTTTTCT
GTTGATGATGTTATAGCATTGAATTTCGTTGATTTGCTTGATTTTTTGGTCACTGTTTAATAGAAATTGTTCAA
GTTTCCAGGTTTGATTAATTGTGTCCTGTGTAGGGATATTTATGATCAAAATTAATCAATTTGAAGAAAACACT
ATGTTTAATGGATAATATATGCTTTTTTATTTTTCTTGTTGATGATGTTATAGTCTTGTATATTCTCGTGTTGT
TCCATTTTCTGTTTTCTATTTGCTTGAAATTGTTCAAGTTTCTAGGTTTGATTATTTGTGTGCTATCTAGGGA
TTTTTGTGATCAAAATTACAAATCTAGGTTAAATGGATGATGCATGCTTTTGCTGCTGATGATTTATAGCCTTG
AATTTTGTCGATTTGCTTCATTTTTGGTCTCTATTTAATGAAATTGTTGAAGTTTCTAGGTTTGATTAATTGTG
TCTTGTCTAGGGTTTTTGCGAACAAATTGAACTAGATTTAAATAAATTTAGGAGTCCTCAATTTTTTTGTTTGT
TAACTCTTATTGATCTGTTTTTTTAATGTATTTATTCTTGTGTGGGCACATTGTTATTCTCTTCTGATTATGCT
ACGATCGTGAACTTGATTTGATTTACAATACATCCAATTGTGGGTTTGCATCCCTCTTAAAATGATAAGTATAG
TTTGTTCTAGGTAGAATTGGATGCTTCTAGGGGCCTACTGATTTGTTTGTAAAAATGGTTGTTCATTGGATTGA
ATTTTTATTAAAGAAAAAATCTGAAATTCTAATAATTCTTGTAAATTAGGTTGATGTCAGATCTATTTATTTTC
TTCTTTGTTTGGTTGACTGGTCTTCTGGTGGCTCTCTGATTAGTGTAATTATAGTTGACTTTGGATATGTTGCT
TTTGCTCTTTGTATGGTTTCTAATCAATTGGGATTCTTTTCTTATTCTCTCCTAATTTGCCTCTGGTTTGATAT
ATTCAATTTTAACTTCAATTGTTTCGTGGGATGACTTGTCCCAAATTAAACAAGTTCTGAGATTTGTGTGCAAG
CTATGCTATGGGTGTTCATATTATGTGGTAGTTCGCTGCTGTAAGAGGGAGATTGCAGAACCTTTATTATATCG
TCTTTTCTTTTTGGACTTCCAAAGCTTGCTAGTTGTCATCTCTGCCTGATTGAATAGAATTTTTGACAGTTGT
GTGCTTGAATATATTTCAGATGCAGATCTTTGTTAAGACACTCACCGGAAAGACCATCACTCTTGAGGTCGAGA
GTTCTGACACCATTGATAATGTCAAAGCTAAGATTCAAGACAAGGAAGGCATTCCTCCAGATCAGCARAGGCTG
ATCTTTGCTGGGAAACAACTTGAAGATGGCCGAACACTTGCTGATTACAACATCCAAAAAGAGTCTACCCTCCA
```

FIG. 2

```
TCTTGTCCTTCGTCTACGTGGTGGAGGATCCCCGGGTGGTCAGTCCCTTATGTTACGTCCTGTAGAAACCCCAA
CCCGTGAAATCAAAAAACTCGACGGCCTGTGGGCATTCAGTCTGGATCGCGAAAACTGTGGAATTGATCAGCGT
TGGTGGGAAAGCGCGTTACAAGAAAGCCGGGCAATTGCTGTGCCAGGCAGTTTTAACGATCAGTTCGCCGATGC
AGATATTCGTAATTATGCGGGCAACGTCTGGTATCAGCGCGAAGTCTTTATACCGAAAGGTTGGGCAGGCCAGC
GTATCGTGCTGCGTTTCGATGCGGTCACTCATTACGGCAAAGTGTGGGTCAATAATCAGGAAGTGATGGAGCAT
CAGGGCGGCTATACGCCATTTGAAGCCGATGTCACGCCGTATGTTATTGCCGGGAAAAGTGTACGTATCACCGT
TTGTGTGAACAACGAACTGAACTGGCAGACTATCCCGCCGGGAATGGTGATTACCGACGAAAACGGCAAGAAAA
AGCAGTCTTACTTCCATGATTTCTTTAACTATGCCGGAATCCATCGCAGCGTAATGCTCTACACCACGCCGAAC
ACCTGGGTGGACGATATCACCGTGGTGACGCATGTCGCGCAAGACTGTAACCACGCGTCTGTTGACTGGCAGGT
GGTGGCCAATGGTGATGTCAGCGTTGAACTGCGTGATGCGGATCAACAGGTGGTTGCAACTGGACAAGGCACTA
GCGGGACTTTGCAAGTGGTGAATCCGCACCTCTGGCAACCGGGTGAAGGTTATCTCTATGAACTGTGCGTCACA
GCCAAAAGCCAGACAGAGTGTGATATCTACCCGCTTCGCGTCGGCATCCGGTCAGTGGCAGTGAAGGGCCAACA
GTTCCTGATTAACCACAAACCGTTCTACTTTACTGGCTTTGGTCGTCATGAAGATGCGGACTTACGTGGCAAAG
GATTCGATAACGTGCTGATGGTGCACGACCACGCATTAATGGACTGGATTGGGGCCAACTCCTACCGTACCTCG
CATTACCCTTACGCTGAAGAGATGCTCGACTGGGCAGATGAACATGGCATCGTGGTGATTGATGAAACTGCTGC
TGTCGGCTTTAACCTCTCTTTAGGCATTGGTTTCGAAGCGGGCAACAAGCCGAAAGAACTGTACAGCGAAGAGG
CAGTCAACGGGGAAACTCAGCAAGCGCACTTACAGGCGATTAAAGAGCTGATAGCGCGTGACAAAAACCACCCA
AGCGTGGTGATGTGGAGTATTGCCAACGAACCGGATACCCGTCCGCAAGTGCACGGGAATATTTCGCCACTGGC
GGAAGCAACGCGTAAACTCGACCCGACGCGTCCGATCACCTGCGTCAATGTAATGTTCTGCGACGCTCACACCG
ATACCATCAGCGATCTCTTTGATGTGCTGTGCCTGAACCGTTATTACGGATGGTATGTCCAAAGCGGCGATTTG
GAAACGGCAGAGAAGGTACTGGAAAAAGAACTTCTGGCCTGGCAGGAGAAACTGCATCAGCCGATTATCATCAC
CGAATACGGCGTGGATACGTTAGCCGGGCTGCACTCAATGTACACCGACATGTGGAGTGAAGAGTATCAGTGTG
CATGGCTGGATATGTATCACCGCGTCTTTGATCGCGTCAGCGCCGTCGTCGGTGAACAGGTATGGAATTTCGCC
GATTTTGCGACCTCGCAAGGCATATTGCGCGTTGGCGGTAACAAGAAAGGGATCTTCACTCGCGACCGCAAACC
GAAGTCGGCGGCTTTTCTGCTGCAAAAACGCTGGACTGGCATGAACTTCGGTGAAAAACCGCAGCAGGGAGGCA
AACAATGAATCAACAACTCTCCTGGCGCACCATCGTCGGCTACAGCCTCGGGAATTGCTACCGAGCTCGAATTT
CCCCGATCGTTCAAACATTTGGCAATAAAGTTTCTTAAGATTGAATCCTGTTGCCGGTCTTGCGATGATTATCA
TATAATTTCTGTTGAATTACGTTAAGCATGTAATAATTAACATGTAATGCATGACGTTATTTATGAGATGGGTT
TTTATGATTAGAGTCCCGCAATTATACATTTAATACGCGATAGAAAACAAAATATAGCGCGCAAACTAGGATAA
ATTATCGCGCGCGGTGTCATCTATGTTACTAGATCGGGAATTGATCCCCGGGTACC
```

SOLANUM BULBOCASTANUM POLYUBIQUITIN BUL427 PROMOTER AND USES THEREOF

FIELD OF THE INVENTION

The invention relates to isolated *Solanum Bulbocastanum* promoter sequences and uses thereof.

BACKGROUND OF THE INVENTION

Plant genetic engineering allows plant breeders to modify the genetic makeup of a plant precisely and predictably. Both alone and in combination with traditional plant breeding techniques, genetic engineering facilitates the creation of improved varieties faster, and with greater ease, than is possible when only traditional plant-breeding techniques are available.

Isolated plant promoters are instrumental for constructing genetically engineered plants. Typically, to produce transgenic plants, an isolated plant promoter is inserted into a vector and operably linked to a heterologous DNA sequence, thereby creating an expression construct. Plant cells are then transformed with the expression construct by any of a number of art recognized methods. The result of transformation is that the plant promoter operably linked to the heterologous DNA, is inserted into the genome of the transformed plant cell, and regulation of the heterologous DNA expression in the transformed plant cell is controlled by the promoter.

There are a variety of different approaches for producing a desired phenotype in a transgenic plant. The chosen approach typically depends on the nature of the heterologous sequences coupled to the isolated plant promoter. For example, expression of a novel gene that is not normally expressed in plant, or in a particular tissue of a plant, may confer a phenotypic change. Alternatively, the expression of a sense or an antisense construct introduced into transgenic plants can cause the inhibition of expression of endogenous plant genes. This inhibition of expression can, in turn, produce a desired phenotypic change.

To facilitate the production of precise phenotypes, it is advantageous to have available a variety of different promoters for the genetic engineering of plants. Unfortunately however, promoter elements capable of directing high levels of transgene expression are difficult to isolate. Thus, such promoters remain limited in number, and as a result, there is a continuing demand for new promoters.

An exemplary plant promoter used for plant genetic engineering is the CaMV 35S promoter. Derived from the cauliflower mosaic virus, the CaMV35S promoter is the promoter of choice for much of plant genetic engineering. Indeed, it is used in almost all genetically modified crops currently grown or tested.

The CaMV 35S promoter is a strong, constitutive promoter which delivers high expression of operably linked genes in almost any type of cell or tissue of a plant, at any developmental stage. But, despite its current popularity, a number of problems associated with use of the CaMV 35S promoter make its use less than ideal. For example, in addition to being protected by patents that limit its use in the commercial sector, use of the CaMV promoter has provoked concerns about the safety of a promoter that is derived from a virus.

Indeed, some consumers, along with a few advocacy groups, have voiced concern about the safety and environmental impact of genetically engineered food products. Typically, concerns about food safety center around the breaking and joining up of otherwise incompatible genetic material, thereby increasing the chances for horizontal transmission to unrelated species. (see e.g., Nowora, T. et al (1999). *Virology* 255, 214-20, Maiss, E., et al (1992). *J. Gen. Virol.* 73, 709-13; Meyer, M and Dessens, J. (1997). *J. Gen. Viol.* 78, 147-51).

Genetic engineering offers tremendous potential for the production of better and more plentiful products. However, genetic engineering is still a fledgling economic force in the commercial food business and so is far from reaching its full potential. Ultimately, the success or failure of genetically engineered foods depends not only on the quality or quantity of what genetically engineered plants can produce, but instead on public acceptance of the products. Therefore, producers of genetically engineered crops need to ensure that the public is comfortable with the safety of their products.

Thus, what is needed in the art, are genetically engineered foods that are readily accepted by the public. To meet the demand for safe acceptable produce, what is needed are promoters that are publicly acceptable and do not provoke safety concerns, and which at the same time, are effective at controlling gene expression and producing desired phenotypes. Such promoters should be capable of directing high levels of transgene expression, should be useful in many different applications, and should be plant derived. Such promoters would avoid or eliminate many if not all of the drawbacks associated with the most popular promoters e.g., CaMV 35S promoter, and thus would facilitate the acceptance of genetically engineered products.

Fortunately, as will be clear from the following disclosure, the present invention provides for these and other needs.

SUMMARY OF THE INVENTION

In one embodiment, the present invention provides an isolated plant Bul427 promoter comprising a nucleic acid sequence that is at least about 90% identical to nucleotides 1-1154 of SEQ ID NO:1, wherein the promoter is capable of controlling transcription in a plant. In another exemplary embodiment, the isolated Bul427 promoter is at least about 95% identical to nucleotides 1-1154 of SEQ ID NO:1. In another exemplary embodiment, the invention provides an isolated plant Bul427 promoter that is capable of hybridizing under stringent conditions to nucleotides 1-1154 of SEQ ID NO:1, and in still another exemplary embodiment, the isolated Bul427 promoter complex has a nucleic acid sequence identical to nucleotides 1-1154 of SEQ ID NO:1.

In another exemplary embodiment, the invention provides a vector comprising an isolated plant Bul427 promoter operably linked to a heterologous nucleic acid sequence.

In another exemplary embodiment, the invention provides a transgenic plant comprising an isolated plant Bul427 promoter operably linked to a heterologous nucleic acid sequence. In one exemplary embodiment, the transgenic plant is a dicotyledonous plant.

In another exemplary embodiment, the invention provides a method for controlling transcription of a heterologous nucleic acid sequence in a plant cell, wherein the method comprises (i) transforming a plant cell with a vector comprising a Bul427 promoter operably linked to a heterologous nucleic acid sequence; and (ii) growing the transformed plant cell under conditions where the heterologous nucleic acid is expressed in the plant cell. In one exemplary embodiment, the method provides constitutive expression of the heterologous nucleic acid. In another exemplary embodiment, expression of the heterologous nucleic acid is upregulated. In still another exemplary embodiment, the expression of the heterologous nucleic acid is upregulated in response to wounding of a plant or plant part comprising the plant cell.

Other features, objects and advantages of the invention will be apparent from the detailed description which follows.

BRIEF DESCRIPTION OF THE DRAWINGS

FIG. 1. SEQ ID NO:1: Sequence of native Bul427 polyubiquitin gene nucleotides 1-5466. Nucleotides 1-1154, promoter; nucleotides 1155-1277, 5' untranslated region; nucleotides 1170-1187, cDNA amplification 5' primeer; nucleotides 1278-2831, intron; nucleotides 2832-4431 six ubiquitin monomers plus interupted seventh ubiquitin monomrt polyprotein; nucleotide 4219-4220, site of two bp deletion relative to full length transcript resulting in a frame shift in seventh ubiquitin monomer; nucleotides 4257-4259 Stop codon Bul427 gene; nucleotides 4432-4434, stop codon in full length transcripts; nucleotides 4435-4581, 3' untranslated similar potato polyubiquitin cDNA tc111734; nucleotides 4505-4538, cDNA amplification 3' primer; nucleotides 5047-5458, 3' untranslated similar to potato S-type kinase cDNA tc81450; nucleotides 5351-5458, S-type kinase psuedogene sequence; nucleotides 5351-5353, stop codon S-type kinase psuedogene.

FIG. 2. SEQ ID NO:2: Sequence of the Bul427-GUS fusion transgene nucleotides 1-5236; nucleotides 1-3059 full length Bul427 promoter sequence; nucleotides 1155-1277, 5' untranslated region; nucleotides 1278-2831 intron; nucleotides 2832-3059, ubiquitin monomer; nucleotides 3060-3065, BamHI Site; nucleotides 3084-4889, *E. coli* β-glucuronidase; nucleotides 4890-4892, stop codon; nucleotides 4960-5210, polyadenylation signal and *Agrobacterium* Nopaline Synthase terminator.

DETAILED DESCRIPTION OF THE INVENTION

Definitions

Figure 3:
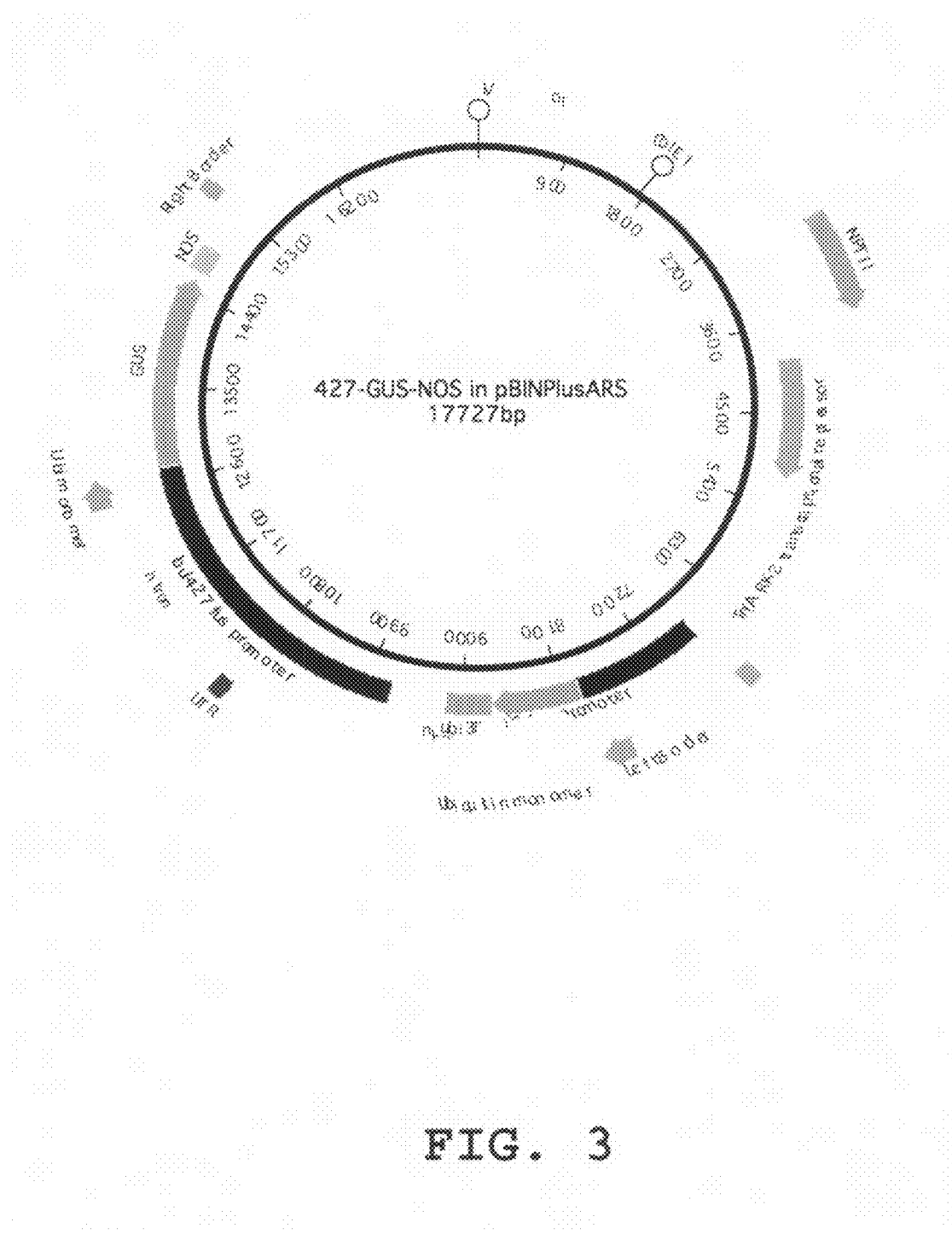
FIG. 3 Bul427 promoter sequence in an expression vector.

The term "plant" as used herein refers to whole plants, plant bodies, plant organs (e.g., leaves, stems, flowers, roots, etc.), seeds, plant tissues, plant cells and progeny of same. In an exemplary embodiment, a plant cell includes callus. In another exemplary embodiment, a plant organ includes a root, a leaf, a flower and/or the like. The term "plant" refers to the broad class of higher plants amenable to transformation techniques. The term "plant" also includes plants of any variety of ploidy levels, including polyploid, diploid, haploid and hemizygous.

Some exemplary plants include, but are not limited to, alfalfa (*Medicago saliva*), sunflower (*Helianthus annus*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), wheat (*Triticum* spp), rice (*Oryza sativa*), barley (*Hordeum vulgare*), oats (*Avena sativa*), maize (*Zea mays*), rye (*Secale cereale*), onion (*Allium* spp), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), papaya (*Carica papaya*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), tomatoes; (*Solanum lycopersicum*), lettuce (e.g., *Lactuea sativa*), carrots (*Caucuis carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* e.g., Hubbard squash (*C. Hubbard*), Butternut squash (*C. moschtata*), Zucchini (*C. pepo*), Crookneck squash (*C. crookneck*), *C. argyrosperma*, *C. argyrosperma* ssp *sororia*, *C. digitata*, *C. ecuadorensis*, *C. foetidissima*, *C. lundelliana*, and *C. martinezii*, and members of the genus *Cucumis* such as cucumber (*Cucumis sativus*), cantaloupe (*C. cantalupensis*), and musk melon (*C. melo*). Ornamental plants e.g., azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and chrysanthemum, and laboratory plants, e.g., *Arabidopsis*.

The term "transgenic plant" as used herein refers to a plant comprising at least one heterologous nucleic acid sequence that was introduced into the plant, at some point in its lineage, by genetic engineering techniques. In an exemplary embodiment, a transgenic plant is a plant that is transformed with an expression vector comprising a Bul427 promoter nucleic acid. In another exemplary embodiment, a transgenic plant is a plant that is the progeny or decendant of a plant that is transformed with an expression vector comprising a Bul427 promoter nucleic acid and which comprises the expression vector comprising a Bul427 promoter nucleic acid. Thus, the term "transgenic plant" refers to plants which are the direct result of transformation with a heterologous nucleic acid or transgene, and the progeny and decendants of transformed plants which comprise the introduced heterologous nucleic acid or transgene.

The terms "isolated," "purified," or "biologically pure" as used herein, refer to material that is substantially or essentially free from components that normally accompany it as found in its native state. In an exemplary embodiment, purity and homogeneity are determined using analytical chemistry techniques such as polyacrylamide gel electrophoresis or high performance liquid chromatography. A nucleic acid that is the predominant species present in a preparation is substantially purified. In one exemplary embodiment, an isolated Bul427 promoter nucleic acid is separated from open reading frames and/or other nucleic acid sequences that flank the Bul427 promoter in its native state. In an exemplary embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examplary analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide" and "protein" are used interchangeably herein to refer to a polymer of amino acid residues. The terms apply to naturally occurring amino acid polymers and non-naturally occurring amino acid polymers as well as amino acid polymers in which one or more amino acid residues is an artificial chemical mimetic of a corresponding naturally occurring amino acid.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art (see, e.g., Creighton, Proteins (1984)). Such conservatively modified variants are in addition to and do not exclude polymorphic variants, interspecies homologs, and alleles.

The following eight groups illustrate some exemplary amino acids that are conservative substitutions for one another:
  1) Alanine (A), Glycine (G);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V);
  6) Phenylalanine (F), Tyrosine (Y), Tryptophan (W);
  7) Serine (S), Threonine (T); and
  8) Cysteine (C), Methionine (M)

Macromolecular structures such as polypeptide structures are described in terms of various levels of organization. For a general discussion of this organization, see, e.g., Alberts et al., Molecular Biology of the Cell ($3^{rd}$ ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "label" as used herein, refers to a composition detectable by spectroscopic, photochemical, biochemical, immunochemical, or chemical means. Exemplary labels include $^{32}$P, fluorescent dyes, electron-dense reagents, enzymes (e.g., as commonly used in an ELISA), biotin, digoxigenin, or haptens and proteins for which antisera or monoclonal antibodies are available.

As used herein a "nucleic acid probe or oligonucleotide" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one exemplary embodiment, probes are directly labeled as with isotopes, chromophores, lumiphores, chromogens etc. In other exemplary embodiments probes are indirectly labeled e.g., with biotin to which a streptavidin complex may later bind. By assaying for the presence or absence of the probe, one can detect the presence or absence of the select sequence or subsequence.

Thus, the term "labeled nucleic acid probe or oligonucleotide" as used herein refers to a probe that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "primer" as used herein, refers to short nucleic acids, typically DNA oligonucleotides of at least about 15 nucleotides in length. In an exemplary embodiment, primers are annealed to a complementary target DNA strand by nucleic acid hybridization to form a hybrid between the primer and the target DNA strand. Annealed primers are then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5©1991, Whitehead Institute for Biomedical Research, Cambridge, Mass.). One of skill in the art will appreciate that the specificity of a particular probe or primer increases with its length. Thus, for example, a primer comprising 20 consecutive nucleotides of a Bul427 promoter complex sequence will anneal to a related target sequence with a higher specificity than a corresponding primer of only 15 nucleotides. Thus, in an exemplary embodiment, greater specificity of a nucleic acid primer or probe, is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Sambrook et al., *Molecular Cloning, A Laboratory Manual* 2nd ed. 1989, Cold Spring Harbor Laboratory; and *Current Protocols in Molecular Biology*, Ausubel et al., eds., 1994, John Wiley & Sons). The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, over expressed, under expressed or not expressed at all.

The term "promoter" or "promoter complex" or "promoter sequence" as used herein refers to an array of nucleic acid expression control sequences that direct transcription of a nucleic acid. As used herein, a "promoter" or "promoter complex" or "promoter sequence" comprises necessary nucleic acid sequences near the start site of transcription, such as, e.g., a polymerase II type promoter, a TATA element etc to "control" transcription of an operably linked nucleic acid. In some exemplary embodiments, a "promoter complex" or "promoter sequence" also includes distal enhancer or repressor elements, which can be, but are not necessarily located as much as several thousand base pairs from the start site of transcription. In other exemplary embodiments, "promoter" or "promoter complex" or "promoter sequence" includes sequences that facilitate transcription of an operably linked heterologous nucleic acid and/or expression of the final protein product of the heterologous nucleic acid e.g., intron sequence and/or intron and ubiquitin monomer sequences as disclosed herein.

As is well known in the art, a "constitutive" promoter is a promoter that is active under most environmental and developmental conditions. An "inducible" promoter is a promoter that is active under environmental or developmental regulation, e.g., upregulation in response to wounding of plant tissues. Promoters may be derived in their entirety from a native gene, may comprise a segment or fragment of a native gene, or may be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. It is further understood that the same promoter may be differentially expressed in different tissues and/or differentially expressed under different conditions.

The term "Bul427 promoter" or "Bul427 promoter sequence" or "Bul427 promoter nucleic acid" or "Bul427 promoter complex" as used herein, refers to isolated plant promoters which comprise a nucleotide sequence identical to or substantially identical to base pairs 1-1154 of SEQ ID NO:1, and which are able to control transcription of operably linked nucleic acids in plants. An exemplary Bul427 promoter is illustrated in FIG. 1. Another exemplary Bul427 promoter is illustrated in FIG. 3. Typically, isolated Bul427 promoter sequences are derived from the Bul427 gene of *Solanum Bulbocastanum* or other members of the Solanaceae family. However, isolated Bul427 promoter sequences can be isolated from any source and/or can be synthetically made, by methods known on the art (see e.g., U.S. Pat. No. 5,942,609) as long as they are substantially identical to Bul427 promoter sequences as disclosed herein. Methods for determining nucleotide sequence identity and "substantial identity" are described below. However, in general, two nucleic acid sequences are considered to be substantially identical when the two molecules or their complements hybridize to each other under stringent hybridization conditions, as described below.

The term "capable of hybridizing under stringent hybridization conditions" as used herein, refers to annealing a first nucleic acid to a second nucleic acid under stringent hybridization conditions (defined below). In an exemplary embodiment, the first nucleic acid is a test sample, and the second nucleic acid is the sense or antisense strand of a Bul427 promoter. Hybridization of the first and second nucleic acids is conducted under standard stringent conditions, e.g., high temperature and/or low salt content, which tend to disfavor hybridization of dissimilar nucleotide sequences.

The expression "control transcription", "controlling transcription" or "control of transcription" or other grammatically equivalent phrases or expressions as used herein refers to the ability of an "expression control sequence" typically a promoter, e.g., a Bul427 promoter, to direct transcription of an operably linked nucleic acid sequence. Methods for testing the activity of promoters and putative promoters in plant cells are known in the art see e.g., L. Szabados et al. (1995) Molecular Breeding 1(4):419-423 and Y. Yang et al. (2000)

The Plant Journal, 22(6): 543-551. A promoter that is "able to control transcription of operably linked nucleic acids in plants" refers to promoters that can direct transcription of an operably linked nucleic acid sequence in a plant cell. In an exemplary embodiment, "controlling transcription" refers to initiating transcription. In another exemplary embodiment, "controlling transcription" refers to up-regulating transcription over a basal constitutive level of transcription.

The term "operably linked" refers to a functional linkage between a nucleic acid expression control sequence (such as e.g., a Bul427 promoter, or array of transcription factor binding sites) and a second nucleic acid sequence, wherein the expression control sequence directs expression e.g., transcription, of the nucleic acid corresponding to the second sequence. In an exemplary embodiment, a promoter e.g., a Bul427 promoter, that is "operably linked" to a heterologous nucleic acid is located upstream of and in-frame with the heterologous nucleic acid.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression cassette" as used herein, refers to a nucleic acid construct, typically generated recombinantly or synthetically, which comprises a series of specified nucleic acid elements that permit transcription of a particular nucleic acid in a host cell. In an exemplary embodiment, an expression cassette comprises a heterologous nucleic acid to be transcribed, operably linked to a promoter e.g., a Bul427 promoter.

Typically, an "expression cassette" is part of an "expression vector". The term "vector" as used herein, refers to nucleic acid capable of replicating in a selected host cell or organism. A vector can replicate as an autonomous structure, or alternatively can integrate into the host cell chromosomes and thus replicate along with the host cell genome. Thus, an "expression vector" is a nucleic acids capable of replicating in a selected host cell or organism e.g., a plasmid, virus, artificial chromosome, nucleic acid fragment, or any suitable construct known in the art, which comprises an "expression cassette".

The term "transformation" as used herein encompasses any and all techniques by which a nucleic acid molecule might be introduced into a cell, including but not limited to, transfection with viral vectors, transformation with plasmid vectors, and introduction of naked DNA by electroporation, lipofection, *Agrobacterium* infection, and particle gun acceleration.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length Bul427 promoter sequence or gene sequence given in a sequence listing, or may comprise a complete Bul427 promoter sequence or gene sequence.

The terms "identical" or percent "identity," in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, the substantial identity exists over a region of the sequences that is at least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An exemplary algorithm for sequence comparison is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984).

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. However, other high stringency hybridization conditions known in the art can be used.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

I. Introduction:

In an exemplary embodiment the invention provides isolated Bul427 promoter sequences which comprise a nucleic acid sequence that is at least about 90% identical to base pairs 1-1154 of SEQ ID NO:1, wherein the promoter is capable of initiating transcription in a plant. In another exemplary embodiment, the isolated Bul427 promoter is at least about 95% identical to base pairs 1-1154 of SEQ ID NO:1. In another exemplary embodiment, the isolated Bul427 promoter has a nucleic acid sequence identical to base pairs 1-1154 of SEQ ID NO:1. In still another exemplary embodiment, the isolated Bul427 promoter hybridizes to base pairs 1-1154 of SEQ ID NO:1 under stringent conditions.

In other exemplary embodiments the invention provides expression vectors comprising isolated Bul427 promoter sequences, transgenic plants comprising isolated Bul427 promoter sequences, and methods for expressing heterologous nucleic acids in plants, wherein the heterologous nucleic acid is operably linked to an isolated Bul427 promoter sequence.

II. Isolating the Polyubiquitin Promoter and Constructing Expression Vectors

A. General Recombinant DNA Methods

This invention utilizes routine techniques in the field of recombinant genetics. Basic texts disclosing the general methods of use in this invention include Sambrook et al., Molecular Cloning—A Laboratory Manual (2nd Ed.), Vol. 1-3, Cold Spring Harbor Laboratory, Cold Spring Harbor, N.Y., 1989; Kriegler, Gene Transfer and Expression: A Laboratory Manual (1990); and Current Protocols in Molecular Biology (Ausubel et al., eds., 1994)). Unless otherwise noted, technical terms are used according to conventional usage. Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Methods for the Isolation of Nucleic Acids Comprising Bul427 Promoter Sequences Plant Bul427 promoters can be isolated using any of a variety of methods known to those of skill in the art which may be used for isolation of plant promoters. For example, plant Bul427 promoters can be isolated from genomic DNA fragments encoding a plant Bul427 gene. The term "plant Bul427 gene" or "Bul427 gene" as used herein, refers to a plant genomic DNA molecule that comprises the entire Bul427 promoter region operably linked to the entire coding region (including exons and introns) for the Bul427 protein and which may also include the adjacent 3' flanking region which encodes the 3' non-translated mRNA. An exemplary "Bul427 gene" is shown in FIG. 1. The term "plant Bul427 gene fragment" or "Bul427 gene fragment" refers to a portion of the plant Bul427 gene which is less than the entire promoter and coding regions of the gene. A plant Bul427 gene fragment may comprise a promoter region operably linked to a portion of the coding region of the gene. An exemplary "plant Bul427 gene fragment" is illustrated in nucleotides 1-3059 of FIG. 2. Genomic fragments encoding plant Bul427 genes and Bul427 gene fragments can be prepared as disclosed below.

In an exemplary embodiment, the nucleic acid sequences comprising Bul427 promoter sequences and related nucleic acid sequences are cloned from genomic DNA libraries using labeled oligonucleotide probes. In another exemplary embodiment, the nucleic acid sequences comprising Bul427 promoter sequences and related nucleic acid sequences are cloned from genomic DNA libraries using amplification techniques and labeled oligonucleotide primers.

Plant Bul427 promoter sequences typically comprise sequences that are identical to, or show substantial sequence identity (as defined above) to nucleotides 1-1154 of the *Solanum bulbocastanum* plant Bul427 promoter nucleic acid sequence depicted in SEQ ID NO:1.

Thus, plant Bul427 promoter sequences typically hybridize to base pairs 1-1154 of the nucleic acid sequence of SEQ ID NO: 1 under stringent hybridization conditions.

To prepare a genomic library, typically DNA is extracted from plant tissue and either mechanically sheared or enzymatically digested to yield fragments of about 15-20 kb. The fragments are then separated by gradient centrifugation from undesired sizes and are constructed in bacteriophage lambda vectors. These vectors and phage are packaged in vitro, as described e.g., in Sambrook, et al. supra. Recombinant phage are analyzed by plaque hybridization as described in Benton and Davis, Science, 196:180-182 (1977). Colony hybridization is carried out as generally described in M. Grunstein et al. Proc. Natl. Acad. Sci. USA., 72:3961-3965 (1975). DNA encoding plant Bul427 genes and/or plant Bul427 gene fragments is identified in genomic libraries by its ability to hybridize with labeled nucleic acid probes that comprise Bul427 promoter sequences, e.g., on Southern blots. The hybridizing DNA regions are isolated by standard methods familiar to those of skill in the art. See e.g., Sambrook, et al. supra.

In an exemplary embodiment, plant Bul427 promoter sequences are isolated by screening plant DNA libraries with labeled oligonucleotide probes having sequences derived from nucleotides 1-1154 of the DNA sequence of the *Solanum bulbocastanum* Bul427 promoter shown in FIG. 1, SEQ ID NO:1.

Other methods known to those of skill in the art can also be used to isolate plant DNA fragments comprising Bul427 promoters. See e.g., Sambrook, et al. for a description of other techniques for the isolation of DNAs related to DNA molecules of known sequence.

In exemplary embodiments, deletion analysis and a promoterless reporter gene (e.g., GUS) are used to identify those regions which can drive expression of a structural gene.

Sequences characteristic of promoter sequences can also be used to identify the promoter. Indeed, sequences controlling eukaryotic gene expression have been extensively studied. For instance, promoter sequence elements include the TATA box consensus sequence (TATAAT), which is usually 20 to 30 base pairs upstream of the transcription start site. In plants, further upstream from the TATA box, at positions −80 to −100, there is typically a promoter element with a series of adenines surrounding the trinucleotide G (or T) N G, see e.g., J. Messing et al., (1983) in Genetic Engineering in Plants, pp. 221-227 Kosage, Meredith and Hollaender, eds.

Once a putative promoter sequence is identified it can be tested for promoter activity, e.g., tested for the ability to direct transcription of an operably linked nucleic acid sequence in plants. Methods for testing the activity of promoters and putative promoters in plant cells are known in the art see e.g., L. Szabados et al. (1995) Molecular Breeding 1(4):419-423 and Y. Yang et al. (2000) The Plant Journal, 22(6): 543-551.

In one exemplary embodiment, plant promoters are characterized in vivo by generating a transgenic plant which comprises an expression vector comprising a putative promoter operably linked to a heterologous nucleic acid that acts as a reporter gene e.g., a nucleic acid encoding GUS activity. The transgenic plant is then evaluated for expression of the reporter gene.

In another exemplary embodiment, *Agrobacterium* mediated transient transfection is used to assay promoter activity see e.g., Y. Yang et al. (2000) supra. As is known in the art *Agrobacterium* mediated transient transfection provides a reliable transient expression assay. Typically, a binary expression vector comprising a putative promoter and an operably linked heterologous reporter gene e.g., GUS, is introduced into an appropriate *Agrobacterium* strain, and the resulting *Agrobacterium* is used to mediate transient transformation in planta, and activity of the reporter gene, e.g., GUS is evaluated by methods well known in the art.

In another exemplary embodiment, ballistic transient transformation of plant cells or organs is used to analyse plant promoter activity (see e.g., Baum, K., et al. (1997). Plant J. 12, 463-469). In still another exemplary embodiment, promoter activity is tested by observing the ability of a nucleic acid sequence to drive the expression of green florescent protein see e.g., Harper, B. K. and Stewart J R. C. N. (2000) *Plant Molecular Biology Reporter* 18: 141a-141i; and Moseyko, N & L. J. Feldman (2001) *Plant, Cell and Environment* 24, 557-563.

Thus, sequences isolated from genomic libraries (or any other source) by virtue of their ability to hybridize to Bul427 promoter sequences, can be tested for promoter activity by methods known in the art.

Sequence Features of Bul427 Promoter Sequences

The full length Bul427 gene from *Solanum bulbocastanum* typically comprises about 4581 nucleotides. The sequence of the full length Bul427 gene is shown in FIG. 1, as SEQ ID NO:1. The—Bul427 promoter from *Solanum bulbocastanum* spans nucleotides 1-1154 of SEQ ID NO:1. The 5' untranslated region spans nucleotides 1231-1353, and an intron is present at nucleotides 1155 through 1277. Nucleotides 2832-4431 encode the six ubiquitin monomers plus interrupted interrupted ubiquitin polyprotein. At nucleotide 4219-4220, there is a two bp deletion relative to full length transcript. A stop codon is present at nucleotides 4257-4259. A 3' untranslated region with sequence similarity to potato polyubiquitin cDNA tc111734 is present at nucleotides 4435-4581. Nucleotides 4505-4538, correspond to a cDNA amplification 3' primer; and at nucleotides 5047-5458a 3' untranslated similar region with sequence similarity to potato S-type kinase cDNA tc81450 is present. At nucleotides 5354-5466 is the S-type kinase psuedogene sequence; and at nucleotides 5351-5353 there is a stop codon for the S-type kinase psuedogene.

In one exemplary embodiment, the Bul427 promoter sequence from *Solanum bulbocastanum*, illustrated in FIG. 2 as nucleotides 1-3059 of SEQ ID NO:2, controls transcription of heterologous nucleic acids in transgenic plants and transgenic plant cell lines wherein the transgenic plant or plant cell line comprises a heterologous nucleic acid operably linked to a full length Bul427 promoter. In another exemplary embodiment, the Bul427 promoter sequence from *Solanum bulbocastanum*, illustrated in FIG. 2 as nucleotides 1-1154 of SEQ ID NO:2, controls transcription of heterologous nucleic acids in transgenic plants and transgenic plant cell lines wherein the transgenic plant or plant cell line comprise a heterologous nucleic acid operably linked to a full length Bul427 promoter.

Various modifications can be made to the Bul427 promoters disclosed herein to provide promoters with different properties (e.g., tissue specificity, promoter strength, and the like). The modified promoters can then be inserted into a suitable vector and tested for their ability to drive expression of a marker gene using methods known in the art see e.g., Y. Yang et al. (2000), supra and other references, supra. Tissue specificity of the modified promoters can be tested in regenerated plants.

C. Construction of Vectors Comprising Bul427 Promoter Sequences

Once a plant Bul427 promoter region has been isolated, various methods may be used to construct expression cassettes, vectors and other DNA constructs. Expression cassettes comprising Bul427 promoter sequence can be constructed in a variety of ways. The skilled artisan is well aware of the genetic elements that must be present on an expression construct/vector in order to successfully transform, select and propagate the expression construct in host cells. Techniques for manipulation of nucleic acids encoding plant Bul427 promoter sequences such as subcloning nucleic acid sequences into expression vectors, labeling probes, DNA hybridization, and the like are described generally in Sambrook, et al., supra.

In an exemplary embodiment, the Bul427 promoter sequence and a heterologous DNA sequence encoding a desired gene product are cloned into an expression vector via suitable restriction endonuclease sites such that the promoter is upstream of and in-frame with the DNA sequence. In another exemplary embodiment, various procedures, such as site directed mutagenesis are used to introduce a restriction site in a Bul427 promoter sequence. In another exemplary embodiment, various procedures, such as site directed mutagenesis are used to introduce a restriction site into heterologous DNA sequence such that the sequence can be cloned into an expression vector downstream from and in-frame with the Bul427 promoter sequence. Thus, heterologous DNA sequences can be linked to the Bul427 promoter such that the expression of the heterologous sequences is controlled by the Bul427 promoter.

DNA constructs comprising a Bul427 promoter operably linked to heterologous DNA sequences can be inserted into a variety of vectors. Typically, the vector chosen is an expression vector that is useful in the transformation of plants and/or plant cells. The expression vector may be a plasmid, virus, cosmid, artificial chromosome, nucleic acid fragment, or the like. Such vectors can be constructed by the use of recombinant DNA techniques well known to those of skill in the art. The expression vector comprising a Bul427 promoter sequence may then be transfected/transformed into the target host cells. Successfully transformed cells are then selected based on the presence of a suitable marker gene as disclosed below.

A number of recombinant vectors are available to those of skill in the art for use in the stable transfection of plant cells or for the establishment of transgenic plants (see e.g., Weissbach and Weissbach, (1989) *Methods for Plant Molecular Biology*, Academic Press; Gelvin et al., (1990) *Plant Molecular Biology Manual; Genetic Engineering of Plants, an Agricultural Perspective*, A. Cashmore, Ed.; Plenum: NY, 1983; pp 29 38; Coruzzi, G. et al., The Journal of Biological Chemistry, 258: 1399 (1983); and Dunsmuir, P. et al., Journal of Molecular and Applied Genetics, 2:285 (1983). As is known in the art, the choice of a vector is influenced by the method that will be used to transform host plants, and appropriate vectors are readily chosen by one of skill in the art. In an exemplary embodiment, known vectors are used to create expression constructs comprising Bul427 promoter sequences.

Typically, plant transformation vectors include one or more cloned plant genes (or cDNAs) operably linked to promoter sequences, e.g., Bul427 promoter sequences, and a selectable marker. Such plant transformation vectors also typically include a transcription initiation start site, a heterologous nucleic acid the control of whose expression is desired, a ribosome binding site, an RNA processing signal, a transcription termination site, and/or a polyadenylation signal.

In some exemplary embodiments, plant transformation vectors may also include additional regulatory sequences from the 3'-untranslated region of plant genes, e.g., a 3' terminator region to increase mRNA stability of the mRNA, such as the PI-II terminator region of potato or the octopine or nopaline synthase (NOS) 3' terminator regions.

(i) Regulatory Elements

In addition to a Bul427 promoter or a derivative thereof, expression constructs prepared as disclosed may comprise additional elements. In an exemplary embodiment, expression constructs comprising a Bul427 promoter operably linked to a heterologous coding region also comprise an enhancer sequence such that the expression of the heterologous protein may be enhanced. As is known in the art, enhancers are typically found 5' to the start of transcription, they can often be inserted in the forward or reverse orientation, either 5' or 3' to the coding sequence. In one exemplary embodiment, the intron region of the Bul427 promoter (bp 831-1365 of SEQ ID NO:1) comprises an enhancer sequence. In one exemplary embodiment, Bul427 promoter sequences are operably linked to a coding sequence in the sense orientation, such that expression with the Bul427 promoter produces the respective sense strand RNA.

In some exemplary embodiments, Bul427 promoter sequences are operably linked to a coding sequence in antisense orientation, such that accumulation of the respective protein encoded by the sense transcript is eliminated or decreased upon expression with the Bul427 promoter.

(ii) Terminators

Expression constructs prepared as disclosed herein typically include a sequence that acts as a signal to terminate transcription and allow for the poly-adenylation of the mRNA produced by coding sequences operably linked to the Bul427 promoter. Termination sequences are typically located in the 3' flanking sequence of a coding sequence, which will typically comprise the proper signals for transcription termination and polyadenylation. Thus, in an exemplary embodiment, termination sequences are ligated into the expression vector 3' of the heterologous coding sequences to provide polyadenylation and termination of the mRNA. Terminator sequences and methods for their identification and isolation are known to those of skill in the art, see e.g., Albrechtsen, B. et al. (1991) Nucleic Acids Res. April 25; 19(8): 1845-1852, and WO/2006/013072. In one exemplary embodiment, the transcription termination sequences comprising the expression constructs, are associated with known genes from the host organism.

(iii) Marker Genes

As noted above, plant transformation vectors typically include a selectable and/or screenable marker gene to allow for the ready identification of transformants. Exemplary selectable marker genes include, but are not limited to those encoding antibiotic resistance (e.g. resistance to hygromycin, kanamycin, bleomycin, G418, streptomycin or spectinomycin) and herbicide resistance genes (e.g., phosphinothricin acetyltransferase). Exemplary screenable markers include e.g., green florescent protein.

In an exemplary embodiment, a selectable or screenable marker gene is employed as, or in addition to, a particular gene of interest, to provide or enhance the ability to identify transformants. As is known in the art, "marker genes" are genes that impart a distinct phenotype to cells expressing the marker gene, such that transformed cells can be distinguished from cells that do not have the marker. In one exemplary embodiment, marker genes encode a selectable marker which one can "select" for by chemical means, e.g., through the use of a selective agent (e.g., a herbicide, antibiotic, or the like). In another exemplary embodiment, marker genes encode a screenable marker, which is identified through observation or testing, e.g., by "screening" (e.g., the green fluorescent protein).

Numerous selectable marker genes are known to the art. Some exemplary selectable markers are disclosed in e.g., Potrykus et al., (1985) Mol. Gen. Genet., 199:183-188; Stalker et al., (1988) Science, 242:419 422; Thillet et al., (1988) J. Biol. Chem., 263:12500 12508; Thompson et al., (1987), EMBO J 6:2519-2523; Deblock et al. (1987), EMBO J. 6:2513-2518; U.S. Pat. No. 5,646,024; U.S. Pat. No. 5,561,236; U.S. Patent application Publication 20030097687; and Boutsalis, P., and Powles, S. B. (1995) Weed Research 35: 149-155.

Some exemplary screenable markers include, but are not limited to a β-glucuronidase (GUS) or uidA gene, see e.g., U.S. Pat. No. 5,268,463, U.S. Pat. No. 5,432,081 and U.S. Pat. No. 5,599,670; a β-gene, see e.g., Sutcliffe, (1978) Proc. Natl. Acad. Sci. USA, 75:3737-3741); β-galactosidase; and luciferase (lux) gene (see e.g., Ow et al., (1986) Science, 234:856-859; Sheen et al., (1995) Plant J., 8(5):777-784; and WO 97/41228).

Exemplary selectable or screenable marker genes also include genes which encode a "secretable marker" whose secretion can be detected as a means of identifying or selecting for transformed cells. Exemplary secretable markers include but are not limited to secretable antigens that can be identified by antibody interaction, e.g., small, diffusible proteins detectable, e.g., by ELISA; and/or secretable enzymes which can be detected by their catalytic activity. E.g., small active enzymes detectable in extracellular solution (e.g., α-amylase, β-lactamase, phosphinothricin acetyltransferase); and proteins that are inserted or trapped in the cell wall (e.g., proteins that include a leader sequence such as that found e.g., in the expression unit of extensin or tobacco PR-S).

The choice of a particular marker gene is readily made by the skilled practitioner according to the needs and considerations of the particular application or use.

(iv) Other Vector Components

In some exemplary embodiments, an expression vector further comprises sequences that are joined to the coding sequence of an expressed heterologous nucleic acid, which are removed post-translationally from the initial translation product. In one exemplary embodiment, post-translationally removed sequences facilitate the transport of the protein into or through intracellular or extracellular membranes, thereby facilitating the transport of the protein into compartments inside and/or outside the cell. In an exemplary embodiment, post-translationally removed sequences protect a nascent protein from intracellular proteolytic degradation. In one exemplary embodiment, a nucleic acid segment encoding a leader peptide sequence upstream and in reading frame with a selected coding sequence is used in recombinant expression of the coding sequence in a host cell.

In another exemplary embodiment, an expression construct comprises a bacterial origin of replication, e.g., a colE1 origin. In still another exemplary embodiment, an expression construct/vector comprises a bacterial selectable marker e.g., an ampicillin, tetracyclin, hygromycin, neomycin or chloramphenicol resistance gene.

As is well known in the art, expression constructs typically comprise restriction endonuclease sites to facilitate vector construction. Exemplary restriction endonuclease recognition sites include, but are not limited to recognition site for the restriction endonucleases NotI, AatII, SacII, PmeI HindIII, PstI, EcoRI, and BamHI.

D. Plant Hosts, Plant Transformation and Plant Selection and Regeneration Techniques DNA constructs containing a Bul427 promoter operably linked to a heterologous DNA sequence can be used to transform plant cells and produce transgenic plants with desired phenotypic characteristics.

Exemplary plants for transformation with expression constructs comprising Bul427 promoter sequences include, but are not limited to; dicotyledonous species, such as e.g., tobacco (*Nicotiana* spp.), tomato (*Solanum* spp.), potato (*Solanum* spp.), hemp (*Cannabis* spp.), sunflower (*Helianthus* spp.), sorghum (*Sorghum vulgare*), wheat (*Triticum* spp.), maize (*Zea mays*), rice (*Oryza sativa*), rye (*Secale cereale*), oats (*Avena* spp.), barley (*Hordeum vulgare*), rapeseed (*Brassica* spp.), broad bean (*Vicia faba*), french bean (*Phaseolus vulgaris*), other bean species (*Vigna* spp.), lentil (*Lens culinaris*), soybean (*Glycine max*), arabidopsis (*Arabidopsis thaliana*), guayule (*Parthenium argentatum*), cotton (*Gossypium hirsutum*), petunia (*Petunia hybrida*), flax (*Linum usitatissimum*), and carrot (*Daucus carota sativa*).

Transformation and regeneration of monocotyledonous and dicotyledonous plant cells is well known in the art, see e.g., Weising et al. Ann. Rev. Genet. 22:421-477 (1988); U.S. Pat. No. 5,679,558; *Agrobacterium Protocols* Kevan M. A. Gartland ed. (1995) Humana Press Inc. and Wang, M., et al. (1998) Acta Hort. (ISHS) 461:401-408. The choice of method varies with the type of plant to be transformed, the particular application and/or the desired result. The appropriate transformation technique is readily chosen by the skilled practitioner.

Exemplary transformation/transfection methods available to those skilled in the art include, but are not limited to: direct uptake of foreign DNA constructs (see e.g., EP 295959); techniques of electroporation (see e.g., Fromm et al., (1986) Nature (London) 319:791) high-velocity ballistic bombardment with metal particles coated with the nucleic acid constructs (see e.g., Kline et al., Nature (London) 327:70 (1987), and U.S. Pat. No. 4,945,050); methods to transform foreign genes into commercially important crops, such as rapeseed (see e.g., De Block et al., Plant Physiol. 91:694 701 (1989)), sunflower (see e.g., Everett et al., Bio/Technology 5:1201 (1987)), soybean (see e.g., McCabe et al., Bio/Technology 6:923 (1988); Hinchee et al., Bio/Technology 6:915 (1988); Chee et al., Plant Physiol. 91:1212 1218 (1989); Christou et al., Proc. Natl. Acad. Sci USA 86:7500 7504 (1989); EP 301749), rice (see e.g., Hiei et al., Plant J. 6:271 282 (1994)), corn (see e.g., Gordon-Kamm et al., Plant Cell 2:603 618 (1990); Fromm et al., Biotechnology 8:833 839 (1990)), and Hevea (see e.g., Yeang, H. Y., et al., In, Engineering Crop Plants for Industrial End Uses. Shewry, P. R., Napier, J. A., David, P. J., Eds.; Portland: London, 1998; pp 55 64). Other known methods are disclosed in e.g., U.S. Pat. Nos. 5,597,945; 5,589,615; 5,750,871; 5,268,526; 5,262,316; and 5,569,831.

Another exemplary method includes: transformation with DNA employing *Agrobacterium tumefaciens* or *Agrobacterium rhizogenes* as the transforming agent, electroporation, particle acceleration, etc. (see, e.g., EP 295959 and EP 138341). In one exemplary embodiment, Ti-derived vectors are used to transform a wide variety of higher plants, including dicotyledonous plants, such as e.g., potato, soybean, cotton, rape, tobacco, and rice (see e.g., Pacciofti et al., Bio/Technology 3:241 (1985); Byrne et al., Plant Cell, Tissue and Organ Culture 8:3 (1987); Sukhapinda et al., Plant Mol. Biol. 8:209 216 (1987); Lorz et al., Mol. Gen. Genet. 199:178 (1985); Potrykus, (1985) supra; Park et al., J. Plant Biol. 38(4):365 71 (1995); and Hiei et al., Plant J. 6:271 282 (1994)).

*Agrobacterium tumefaciens*-meditated transformation techniques are well described in the scientific literature. See, e.g., Horsch et al. Science (1984) 233:496-498, and Fraley et al. (1983) Proc. Natl. Acad. Sci. USA 80:4803. Typically, a plant cell, an explant, a meristem or a seed is infected with *Agrobacterium* tumefaciens transformed with the expression vector/construct which comprises a Bul427 promoter sequence. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (see e.g., Horsch et al., (1984) supra; Fraley et al., (1983) Proc. Nat'l. Acad. Sci. U.S.A. 80:4803).

All plant cells which can be transformed by *Agrobacterium* and whole plants regenerated from the transformed cells can also be transformed so as to produce transformed whole plants which contain the transferred expression vector/construct which comprises a Bul427 promoter sequence.

There are various ways to transform plant cells with *Agrobacterium*, including:

(1) co-cultivation of *Agrobacterium* with cultured isolated protoplasts, (2) transformation of cells or tissues with *Agrobacterium*, or (3) transformation of seeds, apices or meristems with *Agrobacterium*.

Method (1) requires an established culture system that allows culturing protoplasts and plant regeneration from cultured protoplasts. Method (2) requires (a) that the plant cells or tissues can be transformed by *Agrobacterium* and (b) that the transformed cells or tissues can be induced to regenerate into whole plants. Method (3) requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may also be used.

Transformed plant cells which are derived by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in e.g., Evans et al., Protoplasts Isolation and Culture, Handbook of Plant Cell Culture, pp. 124-176, MacMillan Publishing Company, New York, 1983; and Binding, Regeneration of Plants, Plant Protoplasts, pp. 21-73, CRC Press, Boca Raton, 1985, each of which is incorporated herein by reference. Regeneration can also be obtained from plant callus, explants, organs, or parts thereof. Such regeneration techniques are described generally in Klee et al. Ann. Rev. of Plant Phys. 38:467-486 (1987).

One of skill will recognize that, after an expression cassette comprising a Bul427 promoter sequence is stably incorporated in transgenic plants and confirmed to be operable, it can be introduced into other plants by sexual crossing. Any of a number of standard breeding techniques can be used, depending upon the species to be crossed.

The skilled artisan will recognize that different independent transformation events will result in different levels and patterns of expression (Jones et al., EMBO J. 4:2411 2418 (1985); De Almeida et al., Mol. Gen. Genetics 218:78 86 (1989)), and thus that multiple events will likely need to be screened in order to obtain lines displaying the desired expression level and pattern. Exemplary methods for screening transformation events may be accomplished e.g., by Southern analysis of DNA blots (Southern, (1975) J. Mol. Biol. 98: 503), Northern analysis of mRNA expression (Kroczek, J., (1993) Chromatogr. Biomed. Appl., 618(1 2): 133 145), Western analysis of protein expression, and/or phenotypic analysis e.g., resistance to an herbicide can be detected by treatment with the herbicide. Expression of the heterologous DNA can also be detected by measurement of the specific RNA transcription product. This can be done by, for example, RNAse protection or Northern blot procedures. If heterologous DNA sequences encode a novel protein, the protein product may be assayed, for instance, by its function or by a variety of immunoassay techniques. Alternatively, a novel protein product with enzymatic activity can be measured in an enzyme assay. In another exemplary embodiment, protein expression is quantitated and/or detected in different plant tissues using a reporter gene, e.g., GUS.

Once transgenic plants have been obtained, they may be grown to produce plant tissues or parts having the desired phenotype. The plant tissue or plant parts may be harvested, and/or the seed collected. The seed may serve as a source for growing additional plants with tissues or parts having the desired characteristics.

E. Expression of Heterologous Nucleic Acids in Transformed Plants

The introduction of expression vectors into plants and plant cells as disclosed herein is useful for the introduction of one or more new traits to a host plant cell. There are a variety of different approaches one can use to produce a desired phenotype in transgenic plants. In an exemplary embodiment, using methods described herein, one can operably link a heterologous gene to a Bul427 promoter sequence and transform plant cells. Transgenic plants can be produced from the transformed plant cells so that the heterologous gene product is produced in certain tissues (e.g., leaves, fruit) of a transgenic plant. In this context, the term "heterologous gene" refers to a gene that is not normally present in a plant or which, if present, is not normally expressed in a particular plant cell tissue. The expression of the gene can result in the production of a protein that confers an altered phenotype on a transgenic plant. In some exemplary embodiments, a Bul427 promoter sequence operably linked to a heterologous gene is used to create transgenic plants in which heterologous nucleic acid sequences are expressed at higher or lower levels than normal. In another exemplary embodiment a heterologous nucleic acid operably linked to Bul427 promoter sequences, is introduced into a transgenic plant to modify the rate, timing, amount and/or quality of the expression of the heterologous nucleic acid.

A variety of genes capable of altering a plant phenotype can be expressed under control of Bul427 promoter sequences. Suitable genes include, but are not limited to: genes for herbicide resistance; genes for fungal disease resistance (e.g., chitinases and glucanases); genes for bacterial disease resistance (e.g., cecropins); and genes for insect resistance (e.g., *B. thuringiensis* toxin). Since, in some exemplary embodiments, a Bul427 promoter sequence provides injury-regulated as well as general expression, genes affecting fruit development could also be usefully expressed. For example, in an exemplary embodiment, a Bul427 promoter sequence can be operably linked to, e.g., genes for ripening or degradation (e.g., Acc oxidase, Acc synthase, polygalacturonase, phytoene synthase); genes for color; or genes for sweetness.

One of skill will recognize that proteins have different domains which perform different functions. Thus, gene sequences operably linked to a Bul427 promoter sequence need not be full length, so long as the desired functional domain of the protein is expressed. Modified protein chains can also be readily designed utilizing various recombinant DNA techniques well known to those skilled in the art. For example, the chains can vary from the naturally occurring sequence at the primary structure level by amino acid substitutions, additions, deletions, and the like. These modifications can be used in a number of combinations to produce the final modified protein chain.

DNA constructs containing a Bul427 promoter sequence operably linked to a heterologous DNA sequence can also be used in a number of techniques to suppress expression of endogenous plant genes, e.g., sense or antisense suppression. In antisense technology, a nucleic acid segment from the desired plant gene is cloned and operably linked to a Bul427 promoter sequence such that the anti-sense strand of RNA will be transcribed. The construct is then transformed into plants and the anti-sense strand of RNA is produced. In plant cells, it has been shown that anti-sense RNA inhibits gene expression; see, e.g., Sheehy et al., Proc. Nat. Acad. Sci. USA, 85:8805-8809 (1988), and Hiatt et al., U.S. Pat. No. 4,801, 340 which are incorporated herein by reference.

The nucleic acid segment to be introduced in antisense suppression generally will be substantially identical to at least a portion of the endogenous gene or genes to be repressed, but need not be identical. The vectors of the present invention can be designed such that the inhibitory effect applies to other proteins within a family of genes exhibiting homology or substantial homology to the target gene. Segments from a gene can be used (1) directly to inhibit expression of homologous genes in different plant species, or (2) as a means to obtain the corresponding sequences, which can be used to suppress the gene.

The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective. Normally, a sequence of between about 30 or 40 nucleotides and about 2,000 nucleotides is used, though in some exemplary embodiments a sequence of at least about 100 nucleotides is used. In other exemplary embodiments, a sequence of at least about 200 nucleotides is used, and in still other exemplary embodiments, a sequence of at least about 500 nucleotides is used.

In an exemplary embodiment catalytic RNA molecules are expressed under control of a Bul427 promoter sequence. Catalytic RNA molecules or ribozymes also have been reported to have use as a means to inhibit expression of endogenous plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozyme is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *solanum nodiflorum* mottle virus and subterranean clover mottle virus. The design and use of target RNA-specific ribozymes is disclosed in e.g., Haseloff et al. Nature, 334:585-591 (1988).

An exemplary method of suppression is sense suppression. Introduction of a nucleic acid configured in the sense orientation has been shown to be an effective means by which to block the transcription of target genes. For examples of the use of this method to modulate expression of endogenous genes see, Napoli et al., The Plant Cell 2:279-289 (1990), and U.S. Pat. No. 5,034,323. In an exemplary embodiment, sense suppression is used as a method for ripening control (e.g., Acc oxidase or Acc synthase), sweetness control (e.g., ADPG pyrophosphorylase), or color modification (e.g., chalcone synthase); see e.g., U.S. Pat. No. 5,034,323.

Generally, in sense suppression, some transcription of the introduced sequence occurs. The effect may also occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity is useful to exert a more effective repression of expression of the endogenous sequences. Substantially greater identity of more than about 80% is preferred, though about 95% to absolute identity would be most preferred. The effect may be applied to other proteins within a similar family of genes exhibiting homology or substantial homology. Segments from a gene can be used (1) directly to inhibit expression of homologous genes in different plant species, or (2) as a means to obtain the corresponding sequences, which can be used to suppress the gene.

In sense suppression, the introduced sequence whose expression is under transcriptional control of a Bul427 promoter sequence, needing less than absolute identity, also need not be full length, relative to either the primary transcription product or fully processed mRNA. A higher identity in a shorter than full length sequence compensates for a longer, less identical sequence. Furthermore, the introduced sequence need not have the same intron or exon pattern, and identity of non-coding segments may be equally effective. A sequence of a size of at least 50 base pairs is preferred, with greater length sequences being more preferred; see U.S. Pat. No. 5,034,323.

In one exemplary embodiment, the heterologous nucleic acid sequences under regulatory control of the Bul427 promoter sequences are constitutively expressed. In another exemplary embodiment, heterologous nucleic acid sequences under regulatory control of the Bul427 promoter sequences are induced. In still another exemplary embodiment, the heterologous nucleic acid sequences under regulatory control of the Bul427 promoter sequences which are induced are upregulated. In another exemplary embodiment, the heterologous nucleic acid sequences under regulatory control of Bul427 promoter sequences are upregulated in response to wounding.

Figure 5A:
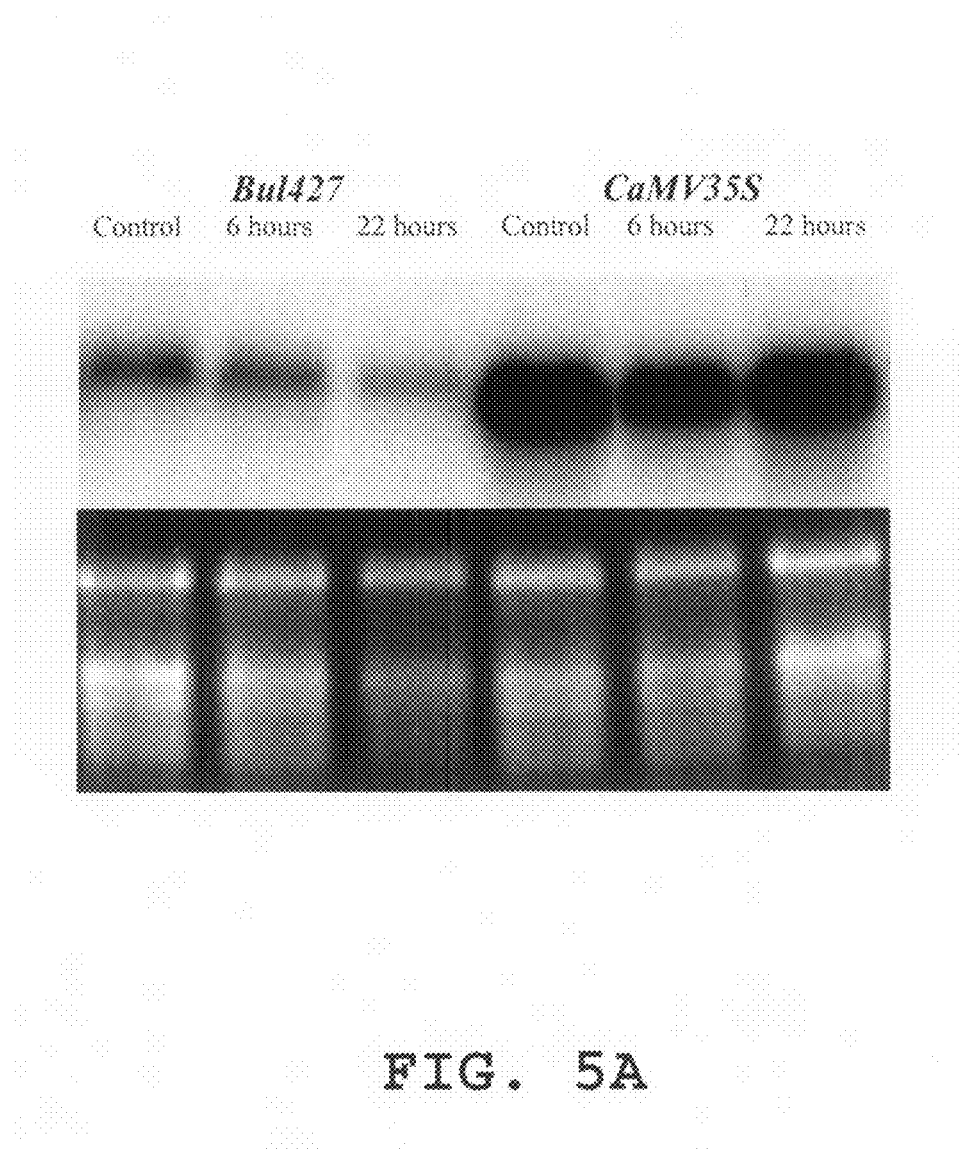
FIG. 5 Wound-induced expression of Bul427-GUS and CaMV35S-GUS in potato leaves (5A), and tubers (5B).

The increase in transgene expression in response to injury (see e.g., FIGS. 5A, and B), provides a means for minimizing or curing disorders associated with plant injury. For example, a variety of economically significant disorders of crop plants are linked to plant injury e.g., in potato, tuber injury can result in bacterial and fungal infection. Thus, directly depositing a heterologous gene product at sites of injury, wherein the gene product protects against diseases and disorders associated with an injury, is but one of many useful applications for which Bul427 promoters are utilized.

Thus, in an exemplary embodiment, an expression vectors comprising a Bul427 promoter operably linked to a heterologous nucleic acid encoding a protective gene product is used to directly deposit the protective gene product at sites of injury. In one exemplary embodiment, a protective gene product is an antimicrobial gene product. Exemplary "antimicrobial gene products" include, but are not limited to: lytic peptides as disclosed in e.g., U.S. Pat. No. 6,084,156; plant antimicrobial peptides (see e.g., Broekaert, W. F., et al. (1997 Crit. Rev. Plant Sci. 16:297-323) and synthetic antimicrobial peptides (see e.g., Bessalle, R., et al. (1993). J. Med. Chem. 36:1203-1209; Arrowood, M. J., et al., (1991) J. Protozool. 38: 161s; and Jaynes, J. M., et al., (1988) FASEB J. 2: 2878).

Kits

In an exemplary embodiment, kits comprising Bul427 expression vectors are provided for expressing heterologous nucleic acids in plant cells. The kits typically include, inter alia, an expression vector comprising a Bul427 promoter and written instructions for using the kit to express heterologous nucleic acid sequences in plants and/or plant cells.

The following examples are offered to illustrate, but not to limit the invention.

EXAMPLES

Example 1

The following example illustrates and exemplary method by which Bul427 promoter sequences are isolated from a bacterial artificial chromosome library. A *Solanum bulb-*

*ocastanum* Bacterial Artificial Chromosome (BAC) library (see e.g., Song, J, F Dong, and J Jiang. (2000) Genome 43: 199-204) was probed with random primed coding sequence from the highly expressed potato polyubiquitin cDNA ubi9 (see e.g., Garbarino, J. E., D. R. Rockhold, and W. R. Belknap (1992) Plant Mol Biol 20: 235-44). Hybridizing BACs were identified and characterized by restriction enzyme analysis. BACs displaying distinct ubiquitin-hybridizing restriction band profiles and patterns indicating a single ubiquitin-hybridizing locus were selected for further characterization. The Bul427 BAC contained and approximately 100 kb insert. The polyubiquitin-hybridizing restriction fragment was subcloned and subjected to sequence analysis. The sequence of the Bul427 polyubiquitin gene is shown in FIG. 1. Pustell matrix analysis (see e.g., Pustell J, Kafatos F C (1982) *Nucleic Acids Res. August* 1982, 11; 10(15):4765-4782 and *Nucleic Acids Res.* (1982) January 11; 10(1):51-59) was used to compare DNA sequences (Mac Vector 8.0). Similar sequences in the available database were identified using the BLAST Network Service of the National Center for Biotechnology Information (see e.g. Altschul et al. 1990 supra).

Example 2

The following example illustrates an exemplary method for the construction of expression vectors comprising Bul427 promoter sequences. An exemplary expression vector comprising Bul427 is shown e.g., in FIG. 3.

A Bul427 expression vector for expression of chimeric genes was constructed. The vector (Bul427-GUS) comprises a full length Bul427 promoter sequence indicated in FIG. 2 and as nucleotides 1-3059 SEQ ID NO:2 operably linked in-frame to an *E. coli* β-glucoronidase (GUS) coding sequence. The promoter illustrated as nucleotides 1-3059 of SEQ ID NO:2 comprises the full-length promoter, intron and first ubiquitin monomer. This construct was initiated by first amplifying the a 3 kb promoter fragment from the bul427 BAC clone using 5' (GCTTGGTCTTACTTCATCGTC, SEQ ID NO:3) and 3' (CCGGATCCTCCACCACGTAGAC-GAAGG, SEQ ID NO:4) primers indicated in FIG. 1 and cloning the product into plasmid pCR2.1. The bul427 promoter product (1278 bp promoter, 1555 bp intron and ubiquitin monomer) was used to construct a GUS translational fusion product with NOS terminator. The 3' end of bul427 (3 kb PCR product contains a BamHI site (both primers contain 5' BamHI sites), the location of the which allows construction of translational fusions identical to those employed previously (see e.g. Garbarino and Belknap (1994) Plant Mol Biol 24(1): 119-27; Garbarino et al. (1995) Plant Physiol 109(4): 1371-1378)). (+). The Bul427-GUS-NOS transgene was constructed in BluescriptII SK(+). The transgene was then mobilized into the binary plant transformation vector pBINPlus/ARS (see e.g., McCue, et al. (2006) Phytochemistry 67(15): 1590-7).

Transgenes were mobilized into potato cv. Lenape via *Agrobacterium*-mediated transformation (see e.g., Snyder and Belknap (1993) Plant Cell Reports 12: 324-327).

Example 3

Figure 4A:
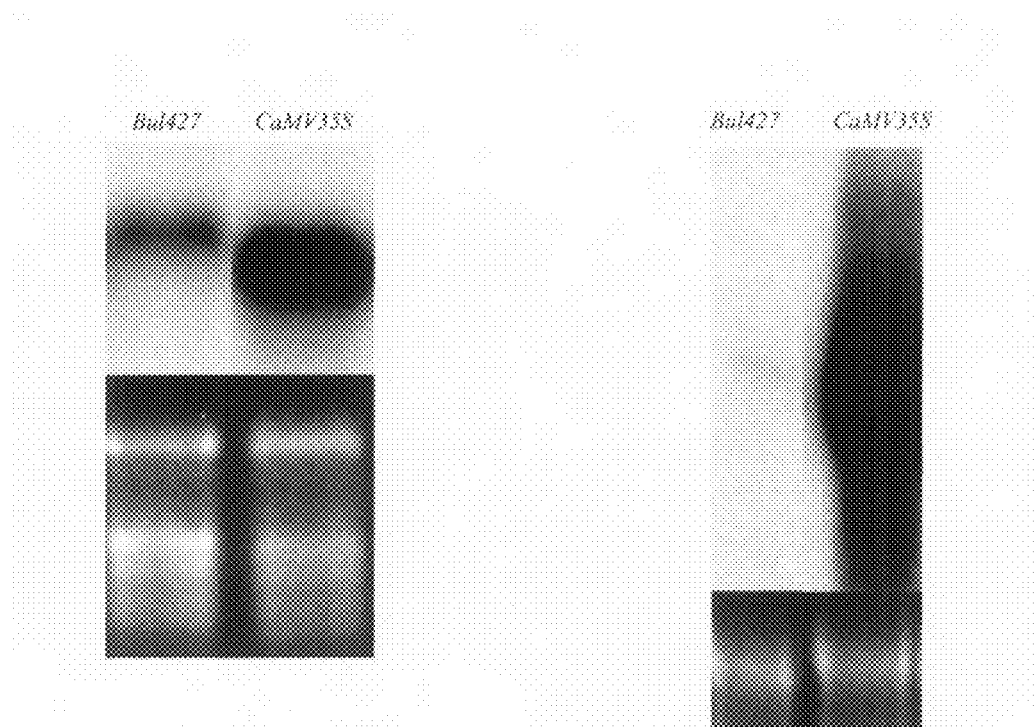
FIG. 4 Control transcription of Bul427-GUS and CaMV35S-GUS in potato leaves (4A) and tubers (4B). GUS activity in control leaves and tubers (4C).
Figure 4B:
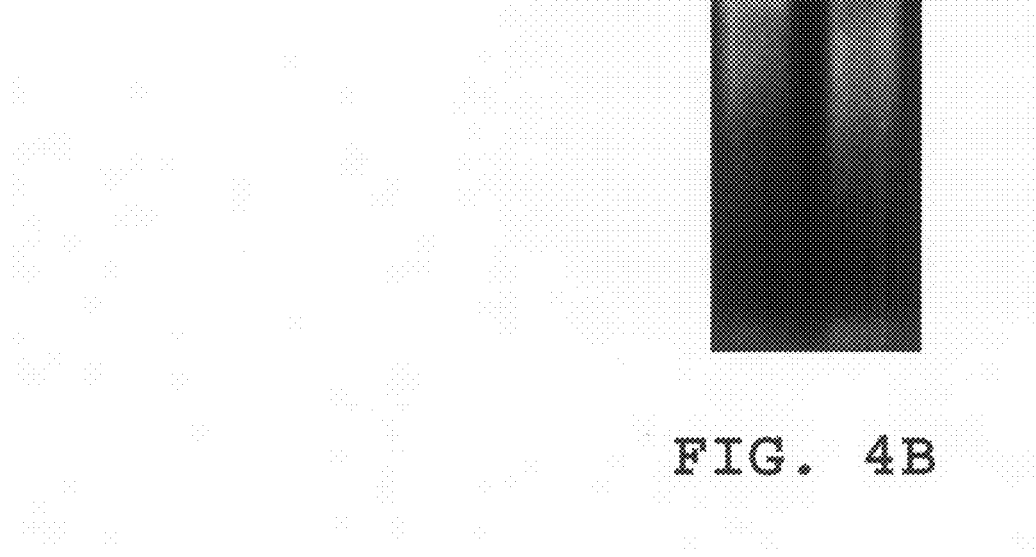
Figure 4C:
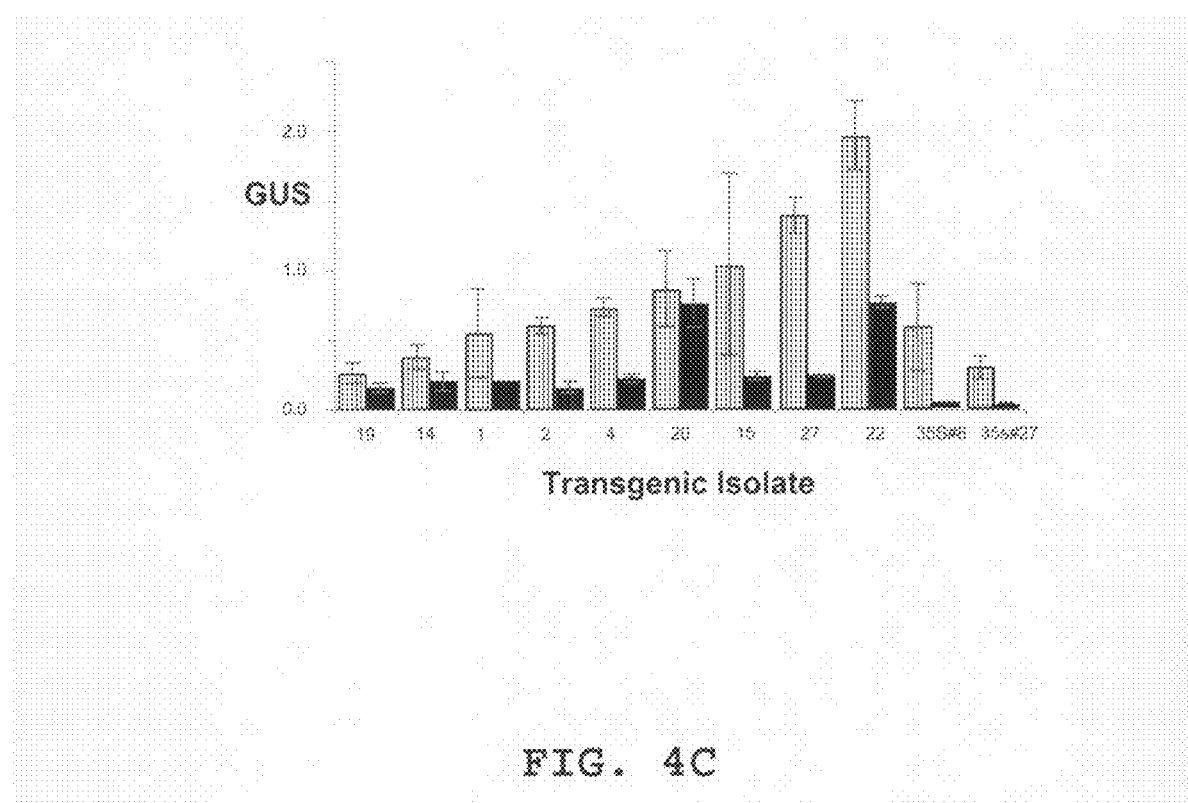

The following example illustrates that Bul427 promoter sequences efficiently control expression of GUS gene sequences when GUS gene sequences are operably linked to a Bul427 promoter sequence. A GUS-Bul427 fusion gene was introduced into potato plant cells by *Agrobacterium* mediated transformation. Expression was then examined in leaves and tubers. The results are shown in FIG. 4. Total RNA was prepared from leaves and tubers. RNA was fractionated by agarose gel electrophoresis, and transferred to a nylon membrane and hybridized with a random primed double stranded GUS probe. FIG. 4A shows expression of GUS sequences in operable linkage to the Bul427 promoter sequence (SEQ ID NO:2 in leaves and FIG. 4B shows expression in tubers. Expression levels of the Bul427 promoter are compared to expression of a corresponding CaMV-GUS fusion.

Example 4

Figure 5B:
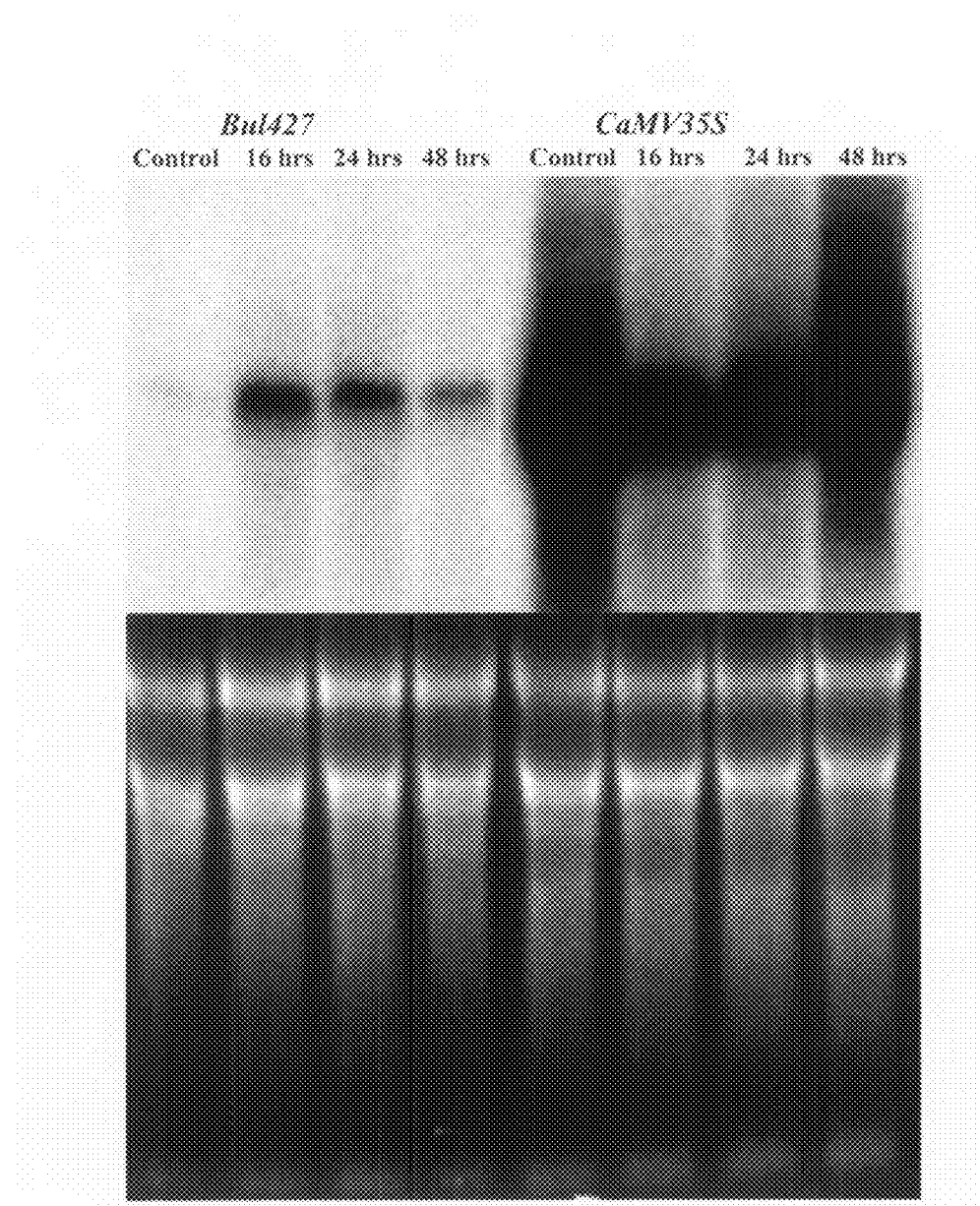

The following example illustrates the induction of expression of a Bul427-GUS fusion gene in response to wounding. The results are shown in FIG. 5.

Potato leaf tissues were wounded using a hemostat and tuber tissues were wounded by cutting into discs as described previously (see e.g., Garbarino and Belknap (1994), supra; Garbarino, et al. (1995), supra). Total RNA was prepared from control and wounded leaves and tubers at times indicated. RNA was fractionated by agarose gel electrophoresis, and transferred to a nylon membrane and hybridized with a random primed double stranded GUS probe In both leaves (FIG. 5A) and tubers (FIG. 5B), expression is significantly increased by wounding, similar to the ubi7 profile (see e.g., Garbarino, et al. (1995) supra).

Example 5

The following example illustrates the relative expression of transgene products in operable linkage to a Bul427 promoter as compared to the CaMV35S promoter.

Transgenic Bul427-GUS (FIG. 2 and SEQ ID NO:2) and CaMV35S-GUS plants were constructed by transforming plants with the expression vector described in Example 2, by methods known in the art (see e.g., Snyder and Belknap (1993) Plant Cell Reports 12: 324-327; Jefferson, et al. (1986) PNAS USA 83(22):8447-8451; Garbarino, et al. 1995, supra). Leaf tissues were taken from 15-week-old plants from the greenhouse. Individual transgenic lines were sampled in triplicate, and assayed for GUS activity (pmol/min/ug protein) as described previously (Jefferson, et al. 1986; Garbarino, et al. 1995, supra). As shown in FIG. 4, in plant leaves the Bul427 promoter out-performed the CaMV35S promoter. Standard deviations were determined using Excel (Microsoft).

The GUS marker gene in the Bul427-GUS (FIG. 2 and SEQ ID NO:2) transgene is transcribed "in frame" with the first ubiquitin monomer, translation of the mature mRNA from this transgene results in the synthesis of a ubiquitin-GUS polyprotein, which is rapidly processed in the plant cell releasing free GUS protein. As is known in the art, this type of translational fusion results in high levels of expression of GUS activity (see e.g., Garbarino, et al. 1995 supra; Hondred Plant Physiol. 119(2): 713-724; Plesse, et al. (2001) Plant Mol. Biol. 45(6):655-657). Results shown in FIG. 4C reveal that in potato leaves GUS activity is much higher when transcription and expression are driven by the Bul427 promoter, than when transcription and expression are driven by the CaMV promoter.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An expression cassette comprising an isolated plant Bul427 promoter, operably linked to a heterologous nucleic acid sequence wherein the isolated plant Bul427 promoter comprises a nucleic acid sequence that is identical to nucleotides 1-1154 of SEQ ID NO:1, and wherein the identity exists over the entire length of the isolated nucleic acid sequence corresponding to nucleotides 1-1154 of SEQ ID NO:1, and wherein the isolated plant Bul427 promoter sequence is capable of controlling transcription in a plant.

2. An expression vector comprising the expression cassette of claim 1.

3. A method for making a transgenic plant, the method comprising:
   (i) transforming a plant, plant part, or plant cell with an expression vector comprising an isolated plant Bul427 promoter operably linked to a heterologous nucleic acid sequence, wherein the isolated plant Bul427 promoter comprises a nucleic acid sequence that is identical to nucleotides 1-1154 of SEQ ID NO:1, and wherein the isolated plant Bul427 promoter is capable of controlling transcription of the heterologous nucleic acid in a plant,
   (ii) selecting transformants comprising the expression vector which comprises the isolated plant Bul427 promoter operably linked to a heterologous nucleic acid sequence, and
   (ii) growing the transformed plant, plant part, or plant cell into a whole plant,
thereby producing a transgenic plant.

4. The method of claim 3, wherein the method further comprises:
   (iv) conducting a sexual cross with the transgenic plant,
   (v) obtaining seed from the sexual cross,
   (vi) growing the seed from the sexual cross, and
   (vii) selecting plants grown from the seed of the sexual cross which comprise the expression vector comprising the Bul427 promoter sequence operably linked to a heterologous nucleic acid sequence,
thereby producing a transgenic plant.

5. A transgenic plant comprising an isolated plant Bul427 promoter operably linked to a heterologous nucleic acid sequence wherein the promoter comprises a nucleic acid sequence that is identical to nucleotides 1-1154 of SEQ ID NO:1, wherein the identity exists over the entire length of the isolated nucleic acid sequence corresponding to nucleotides 1-1154 of SEQ ID NO:1, and wherein the isolated plant Bul427 promoter sequence is capable of controlling transcription in a plant.

6. The transgenic plant of claim 5, wherein the plant is a dicotyledonous plant.

7. The transgenic plant of claim 6, wherein the dicotyledonous plant is a member selected from the group consisting of: alfalfa (*Medicago saliva*), sunflower (*Helianthus annus*), soybean (*Glycine max*), tobacco (*Nicotiana tabacum*), potato (*Solanum tuberosum*), peanuts (*Arachis hypogaea*), cotton (*Gossypium hirsutum*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), tomatoes; (*Solanum lycopersicum*), and lettuce (e.g., *Lactuea sativa*).

8. Transgenic descendants of the transgenic plant of claim 5, where the transgenic descendants comprise the isolated plant Bul427 promoter operably linked to the heterologous nucleic acid sequence.

9. A method for controlling transcription of a heterologous nucleic acid sequence in a plant or plant cell, the method comprising:
   (i) transforming a plant or plant cell with an expression vector comprising an isolated plant Bul427 promoter operably linked to the heterologous nucleic acid sequence, wherein the isolated plant Bul427 promoter comprises a nucleic acid sequence that is identical to nucleotides 1-1154 of SEQ ID NO:1 thereby producing a transformed plant or plant cell; and
   (ii) growing the transformed plant or plant cell under conditions where the isolated plant Bul427 promoter controls transcription of the heterologous nucleic acid in the plant or plant cell.

10. The method of claim 9, wherein the transcription of the heterologous nucleic acid is induced.

11. The method of claim 10, wherein the transcription is induced in response to wounding of a plant or plant part which comprises the transformed plant cell.

12. The method of claim 11, wherein the heterologous nucleic encodes an antimicrobial gene product.

13. The method of claim 9, wherein the transcription of the heterologous nucleic acid up-regulates the expression of an endogenous nucleic acid.

14. The method of claim 9, wherein the transcription of the heterologous nucleic acid down-regulates the expression of an endogenous nucleic acid.

15. The expression cassette of claim 1, wherein the nucleic acid sequence is nucleotides 1-3059 of SEQ ID NO:2.

16. The transgenic plant of claim 5, wherein the nucleic acid sequence is nucleotides 1-3059 of SEQ ID NO:2.

17. The expression cassette of claim 1, wherein the isolated plant Bul427 promoter is nucleotides 1-3059 of SEQ ID NO:2.

* * * * *

SEQUENCE LISTING

<160> NUMBER OF SEQ ID NOS: 4

<210> SEQ ID NO 1
<211> LENGTH: 5466
<212> TYPE: DNA
<213> ORGANISM: Solanum bulbocastanum

<400> SEQUENCE: 1

| | | | | | |
|---|---|---|---|---|---|
| gcttggtctt | acttcatcgt | cgagaaaaga | aagaagactt | ctatctacaa | gtttaactca | 60 |
| aacgtagttc | ttttattttt | ttgggtgtga | agtagtgtca | aaccaaaata | ccctttctaa | 120 |
| acaactattg | tttgtgaata | taggttgtgt | tgtttctcat | tcggaagacc | aagtcccaca | 180 |
| cccttaaact | tcactgatga | gaacaacctc | cgcactctgg | gctgtttaaa | tccccggttg | 240 |
| aaatcatcca | accaaactct | ctttatttcg | agattgaaaa | ggtcgatcaa | ttatgatcaa | 300 |
| agataatgcc | tagtggcgac | gagcccacta | ggaagacctt | tgattacaaa | ggttaccgtg | 360 |
| gtctaggttt | ataatggatt | caattaatca | aagtgcctcc | aactcaatca | aagctcattt | 420 |
| tcctatcagg | agaaaacaat | gcataaaaaa | gggatggccg | tcaaaaagcc | gaccettcaa | 480 |
| tccaaaagcg | ttcaaattcc | cgcctacatc | agctcgacct | gtttgttcgc | tctaattagg | 540 |
| atcatcagaa | tatcttgaca | gattttttg  | aaaagcttaa | cttgcaagcg | gagaatgccg | 600 |
| agtctctacc | cacttttga  | gcttgcaaag | tagcaatatg | aaatttcttg | ggcacttacc | 660 |
| cgtcgtgctt | gagatctaaa | ctgcttacaa | caaccttgac | ctggtccaat | gaaaagagaa | 720 |
| agacttaaag | agctccctct | ataggtgact | cctccaataa | gactcttagg | gtgcatgtca | 780 |
| aaacccgcta | agttaggagt | atacataaaa | ttttggccga | tataaggatt | aatataacca | 840 |
| aataatataa | cgaaaataaa | tttaaacaat | aaaaaataat | aaagagatgt | atccattctt | 900 |
| tttcactcaa | attgtatttt | tagaaattat | agtcaaattt | actatcaaaa | tttaaaaaat | 960 |
| taatttttaa | aattatacat | gccatgaatt | tgaaatttga | aaaagggaaa | aagaggagaa | 1020 |
| gcatctagta | aggctctaat | taattgcgta | accgtgtctt | ctaaaatatc | cgaagaaatt | 1080 |
| gcgtaagcgc | tgagccatag | gcccatacgt | tccctctctg | tgacggcaaa | gcggttacta | 1140 |
| taaatacaga | tcttcccttt | tcaaccaaa  | tccccaaatc | atcatcctttc | tctagcgcaa | 1200 |
| cttctctcgg | aaaaaagcat | ctcctcctcc | tctcgttttc | tcgataatct | ccttgtacac | 1260 |
| tgtttcttct | tctcaaggta | atggtctttt | cttctctcga | ttcaatcgtt | tgttgaagtg | 1320 |
| atttagattt | atgcaggttt | ttgtattata | aatgtatgaa | cagaattata | tgaacggaat | 1380 |
| ttacctttgt | ttcttgttta | tcgatcagat | ctgcacggaa | ttagtcgatt | tgagaacttt | 1440 |
| ttgaaatcga | tgatgtatgt | tttttctgtt | gatgatgcta | tagcgtttaa | tttcgtttga | 1500 |
| tttgctcttg | ttttggtttc | catatggtcg | aattgttgaa | gtttcgtagt | ttgattagtt | 1560 |
| ttgtatccta | tctagggttt | tttgtgatca | caattaatca | atttgaaatg | gtgatgcttg | 1620 |
| cttttctgt  | tgatgatgtt | atagcattga | atttcgttga | tttgcttgat | tttttggtca | 1680 |
| ctgtttaata | gaaattgttc | aagtttccag | gtttgattaa | ttgtgtcctg | tgtagggata | 1740 |
| tttatgatca | aaattaatca | atttgaagaa | aacactatgt | ttaatggata | atatatgctt | 1800 |
| ttttattttt | cttgttgatg | atgttatagt | cttgtatatt | ctcgtgttgt | tccattttc  | 1860 |
| tgttttctat | ttgcttgaaa | ttgttcaagt | ttctaggttt | gattatttgt | gtgctatcta | 1920 |
| gggattttg  | tgatcaaaat | tacaaatcta | ggttaaatgg | atgatgcatg | cttttgctgc | 1980 |
| tgatgattta | tagccttgaa | ttttgtcgat | ttgcttcatt | tttggtctct | atttaatgaa | 2040 |
| attgttgaag | tttctaggtt | tgattaattg | tgtcttgtct | agggttttg  | cgaacaaatt | 2100 |

```
gaactagatt taaataaatt taggagtcct caattttttt gtttgttaac tcttattgat    2160
ctgttttttt aatgtattta ttcttgtgtg ggcacattgt tattctcttc tgattatgct    2220
acgatcgtga acttgatttg atttacaata catccaattg tgggtttgca tccctcttaa    2280
aatgataagt atagtttgtt ctaggtagaa ttggatgctt ctaggggcct actgatttgt    2340
ttgtaaaaat ggttgttcat tggattgaat ttttattaaa gaaaaatct gaaattctaa     2400
taattcttgt aaattaggtt gatgtcagat ctatttattt tcttctttgt ttggttgact    2460
ggtcttctgg tggctctctg attagtgtaa ttatagttga ctttggatat gttgcttttg    2520
ctctttgtat ggtttctaat caattgggat tcttttctta ttctctccta atttgcctct    2580
ggtttgatat attcaatttt aacttcaatt gtttcgtggg atgacttgtc ccaaattaaa    2640
caagttctga gatttgtgtg caagctatgc tatgggtgtt catattatgt ggtagttcgc    2700
tgctgtaaga gggagattgc agaacctta ttatatcgtc ttttcttttt ggacttccaa     2760
agcttgctag tttgtcatct ctgcctgatt gaatagaatt tttgacagtt gtgtgcttga    2820
atatatttca gatgcagatc tttgttaaga cactcaccgg aaagaccatc actcttgagg    2880
tcgagagttc tgacaccatt gataatgtca aagctaagat tcaagacaag gaaggcattc    2940
ctccagatca gcagaggctg atctttgctg ggaaacaact tgaagatggc cgaacacttg    3000
ctgattacaa catccaaaaa gagtctaccc tccatcttgt ccttcgtcta cgtggtggaa    3060
tgcaaatctt tgttaaaact ctgaccggaa agactataac tcttgaggtc gagagttcag    3120
acaccattga taatgtcaaa gctaagattc aagacaagga aggtattccc ccagaccagc    3180
agaggctgat ctttgctggg aaacagcttg aagatggccg aacacttgcg gattacaaca    3240
tccaaaagga gtccaccctt caccttgtcc ttcgccttcg tggtggtatg cagatcttcg    3300
tcaagacact tactggaaag accatcaccc ttgaagttga aagttcagat acaattgaca    3360
acgtaaaggc caaaattcag gataaggaag ggattcctcc agaccagcag agactgatct    3420
ttgccggcaa gcaacttgag gatggaagga ccctggctga ctacaatatt cagaaagagt    3480
ctaccttaca tcttgttctt cgtctgaggg gtggcatgca aatatttgtt aagacattga    3540
cagggaagac aattactttg gaggttgaga gttcagatac tatcgacaat gttaaagcaa    3600
agatccaaga caaggagggt attcctccag accagcagag attgatcttt gctggaaagc    3660
aacttgagga tggaaggacc ttggcggatt acaacattca gaaagaatca accctgcacc    3720
ttgttcttcg ccttagaggt ggcatgcaaa ttttgtcaa gactttgacg gggaagacaa     3780
ttactttgga ggttgagagt tccgatacca ttgacaacgt caaagcaaag attcaagaca    3840
aggagggtat tcccccagac cagcagagat tgatctttgc tggaaagcaa cttgaagatg    3900
gaaggacctt ggcagattac aacattcaga aagaatcaac cctgcacctt gttcttcgcc    3960
ttagaggtgg catgcaaatt tttgtcaaga ctttgactgg gaagacaatt acattggagg    4020
ttgagagttc cgataccatt gacaacgtca agcaaagat tcaagacaag gagggtattc      4080
ccccagacca gcagcgtttg atatttgctg gtaaacaact tgaggacggg aggactcttg    4140
cagactataa catccagaag gagtcaactc tccatttggt gttgcgcttg agaggaggga    4200
tgcagatctt tgtgaagact gactgggaag acaatcacat tggaggtgga gagctctgat    4260
actattgaca atgtgaaagc aaagatacag gacaaggaag ggatcccacc agatcaacag    4320
aggcttatct ttgctggtaa gcagcttgag gatggtcgca cccttgcaga ctacaatatc    4380
cagaaagagt ctactcttca tcttgtcctc aggctccgtg gcggggactt ctgaatgtcc    4440
tgtgtgcttt gttgtttat ttccagactc aagtgttttt cgttgtagtt ctatctttct     4500
```

-continued

```
tttaagagac cttgtaatgt gttatgttct gttgttttttg ttgcaaccta aataaataaa    4560
gattagccga taaatgtgtt gcattgtgaa cttaacacac actctcaccc tccccccctt    4620 ctccccccccc ccccccccccg cgtcacacgc acacactcat gactctgcag gcacagggaa   4680
aagaaggcat ttttttacagt ttgagaacac caatagttct ttttgcaaaa aaacagtatt    4740
atggtggtgg tttggtaata ctctgctaat agtgaagagt tctacccttg atctacgccg    4800
tcttcttatt ttgtaacaat tcttttatta aaaggtggat gtaaggacat cattttaatc    4860
ggttcactaa atactttcca acaatttttt ttttgttaaa aaaagcgcca gaggagaaac    4920
tctctgcata tctagaggat ctctagacta tggacgaaag ctttgtttgt gaggacggac    4980
tcctgaccat gggcaacatg agtcgtggtt gtcgcagatc cccttttcgct atagaggaac    5040 ctgtgagtct tctgaattag tatttacaat tcaaatgcta caacaatggt tgctagtcac    5100
ttagacaaaa tatagtttca ttgtactaca tgtaaatttg aagcaaagtg ttgatatgga    5160
caaatttcaa aatggaaaca gatccactcc agaagataaa tccatgtagt tctgtcaact    5220
ggtggctcta agaggtggag aatgatgtag aaatttgata cattatgatg aagtactccg    5280
ctctctatgg ggaaaattgg ggatacttga aacttaagta caagaaacaa taagtgaaga    5340
agtttagaac tatatggcac ttaaaaaaga agtaggacta ggaggcactg gaatatctac    5400 tgtcccttttc agcatcagta gaactttctt ctgtgaatga ggaatctgga gatgcctaac    5460
accaat                                                               5466

<210> SEQ ID NO 2
<211> LENGTH: 5236
<212> TYPE: DNA
<213> ORGANISM: Artificial Sequence
<220> FEATURE:
<223> OTHER INFORMATION: Bu1427-GUS

<400> SEQUENCE: 2
gcttggtctt acttcatcgt cgagaaaaga aagaagactt ctatctacaa gtttaactca     60
aacgtagttc tttttatttttt ttgggtgtga agtagtgtca aaccaaaata cccttttctaa   120 acaactattg ttttgtgaata taggttgtgt tgtttctcat tcggaagacc aagtcccaca    180
cccttaaact tcactgatga gaacaacctc cgcactctgg gctgtttaaa tccccggttg    240
aaatcatcca accaaactct cttttatttcg agattgaaaa ggtcgatcaa ttatgatcaa    300
agataatgcc tagtggcgac gagcccacta ggaagacctt tgattacaaa ggttaccgtg    360
gtctaggttt ataatggatt caattaatca aagtgcctcc aactcaatca aagctcattt    420
tcctatcagg agaaaacaat gcataaaaaa gggatggccg tcaaaaagcc gacccttcaa    480
tccaaaagcg ttcaaattcc cgcctacatc agctcgacct gtttgttcgc tctaattagg    540
atcatcagaa tatcttgaca gattttttttg aaaagcttaa cttgcaagcg gagaatgccg    600
agtctctacc cacttttttga gcttgcaaag tagcaatatg aaattcttg ggcacttacc    660 cgtcgtgctt gagatctaaa ctgcttacaa caaccttgac ctggtccaat gaaaagagaa    720
agacttaaag agctccctct ataggtgact cctccaataa gactcttagg gtgcatgtca    780
aaacccgcta agtaggagt atacataaaa ttttggccga tataaggatt aatataacca    840
aataatataa cgaaaataaa tttaaacaat aaaaaataat aaagagatgt atccattctt    900
tttcactcaa attgtatttt tagaaattat agtcaaattt actatcaaaa tttaaaaaat    960 taattttttaa aattatacat gccatgaatt tgaaatttga aaaagggaaa aagaggagaa   1020
gcatctagta aggctctaat taattgcgta accgtgtctt ctaaaatatc cgaagaaatt   1080
```

```
gcgtaagcgc tgagccatag gcccatacgt tccctctctg tgacggcaaa gcggttacta    1140
taaatacaga tcttcccttt ttcaaccaaa tccccaaatc atcatccttc tctagcgcaa    1200
cttctctcgg aaaaaagcat ctcctcctcc tctcgttttc tcgataatct ccttgtacac    1260
tgtttcttct tctcaaggta atggtctttt cttctctcga ttcaatcgtt tgttgaagtg    1320
atttagattt atgcaggttt tgtattata aatgtatgaa cagaattata tgaacggaat    1380
ttacctttgt ttcttgttta tcgatcagat ctgcacggaa ttagtcgatt tgagaacttt    1440
ttgaaatcga tgatgtatgt ttttctgtt gatgatgcta tagcgtttaa tttcgtttga    1500
tttgctcttg ttttggtttc catatggtcg aattgttgaa gtttcgtagt ttgattagtt    1560
ttgtatccta tctagggttt tttgtgatca caattaatca atttgaaatg gtgatgcttg    1620
ctttttctgt tgatgatgtt atagcattga atttcgttga tttgcttgat ttttggtca    1680 ctgtttaata gaaattgttc aagtttccag gtttgattaa ttgtgtcctg tgtagggata    1740
tttatgatca aaattaatca atttgaagaa aacactatgt ttaatggata atatatgctt    1800 ttttatttt cttgttgatg atgttatagt cttgtatatt ctcgtgttgt tccatttttc    1860
tgttttctat ttgcttgaaa ttgttcaagt ttctaggttt gattatttgt gtgctatcta    1920 gggattttg tgatcaaaat tacaaatcta ggttaaatgg atgatgcatg cttttgctgc    1980
tgatgattta tagccttgaa ttttgtcgat ttgcttcatt tttggtctct atttaatgaa    2040
attgttgaag tttctaggtt tgattaattg tgtcttgtct agggttttg cgaacaaatt    2100 gaactagatt taaataaatt taggagtcct caatttttt gtttgttaac tcttattgat    2160
ctgttttttt aatgtattta ttcttgtgtg ggcacattgt tattctcttc tgattatgct    2220
acgatcgtga acttgatttg atttacaata catccaattg tgggtttgca tccctcttaa    2280
aatgataagt atagtttgtt ctaggtagaa ttggatgctt ctaggggcct actgatttgt    2340
ttgtaaaaat ggttgttcat tggattgaat ttttattaaa gaaaaaatct gaaattctaa    2400
taattcttgt aaattaggtt gatgtcagat ctatttattt tcttctttgt ttggttgact    2460
ggtcttctgg tggctctctg attagtgtaa ttatagttga ctttggatat gttgcttttg    2520
ctctttgtat ggtttctaat caattgggat tcttttctta ttctctccta atttgcctct    2580
ggtttgatat attcaatttt aacttcaatt gtttcgtggg atgacttgtc ccaaattaaa    2640
caagttctga gatttgtgtg caagctatgc tatgggtgtt catattatgt ggtagttcgc    2700
tgctgtaaga gggagattgc agaacccttta ttatatcgtc ttttcttttt ggacttccaa    2760
agcttgctag tttgtcatct ctgcctgatt gaatagaatt tttgacagtt gtgtgcttga    2820
atatatttca gatgcagatc tttgttaaga cactcaccgg aaagaccatc actcttgagg    2880
tcgagagttc tgcaccatt gataatgtca aagctaagat tcaagacaag gaaggcattc    2940
ctccagatca gcaraggctg atctttgctg ggaaacaact tgaagatggc cgaacacttg    3000
ctgattacaa catccaaaaa gagtctaccc tccatcttgt ccttcgtcta cgtggtggag    3060
gatccccggg tggtcagtcc cttatgttac gtcctgtaga aaccccaacc cgtgaaatca    3120
aaaaactcga cggcctgtgg gcattcagtc tggatcgcga aaactgtgga attgatcagc    3180
gttggtggga agcgcgtta caagaaagcc gggcaattgc tgtgccaggc agttttaacg    3240
atcagttcgc cgatgcagat attcgtaatt atgcgggcaa cgtctggtat cagcgcgaag    3300
tctttatacc gaaaggttgg gcaggccagc gtatcgtgct gcgtttcgat gcggtcactc    3360
attacggcaa agtgtgggtc aataatcagg aagtgatgga gcatcagggc ggctatacgc    3420
catttgaagc cgatgtcacg ccgtatgtta ttgccgggaa aagtgtacgt atcaccgttt    3480
```

-continued

```
gtgtgaacaa cgaactgaac tggcagacta tcccgccggg aatggtgatt accgacgaaa      3540
acggcaagaa aaagcagtct tacttccatg atttctttaa ctatgccgga atccatcgca      3600
gcgtaatgct ctacaccacg ccgaacacct gggtggacga tatcaccgtg gtgacgcatg      3660
tcgcgcaaga ctgtaaccac gcgtctgttg actggcaggt ggtggccaat ggtgatgtca      3720
gcgttgaact gcgtgatgcg gatcaacagg tggttgcaac tggacaaggc actagcggga      3780
ctttgcaagt ggtgaatccg cacctctggc aaccgggtga aggttatctc tatgaactgt      3840
gcgtcacagc caaaagccag acagagtgtg atatctaccc gcttcgcgtc ggcatccggt      3900
cagtggcagt gaagggccaa cagttcctga ttaaccacaa accgttctac tttactggct      3960
ttggtcgtca tgaagatgcg gacttacgtg gcaaaggatt cgataacgtg ctgatggtgc      4020
acgaccacgc attaatggac tggattgggg ccaactccta ccgtacctcg cattacccctt     4080 acgctgaaga gatgctcgac tgggcagatg aacatggcat cgtggtgatt gatgaaactg      4140
ctgctgtcgg ctttaacctc tctttaggca ttggtttcga agcgggcaac aagccgaaag      4200
aactgtacag cgaagaggca gtcaacgggg aaactcagca agcgcactta caggcgatta      4260
aagagctgat agcgcgtgac aaaaaccacc caagcgtggt gatgtggagt attgccaacg      4320
aaccggatac ccgtccgcaa gtgcacggga atatttcgcc actggcggaa gcaacgcgta      4380
aactcgaccc gacgcgtccg atcacctgcg tcaatgtaat gttctgcgac gctcacaccg      4440
ataccatcag cgatctcttt gatgtgctgt gcctgaaccg ttattacgga tggtatgtcc      4500
aaagcggcga tttggaaacg gcagagaagg tactggaaaa agaacttctg gcctggcagg      4560
agaaactgca tcagccgatt atcatcaccg aatacggcgt ggatacgtta gccgggctgc      4620
actcaatgta caccgacatg tggagtgaag agtatcagtg tgcatggctg gatatgtatc      4680
accgcgtctt tgatcgcgtc agcgccgtcg tcggtgaaca ggtatggaat ttcgccgatt      4740
ttgcgacctc gcaaggcata ttgcgcgttg gcgtaacaa gaaagggatc ttcactcgcg      4800
accgcaaacc gaagtcggcg gctttttctgc tgcaaaaacg ctggactggc atgaacttcg      4860
gtgaaaaacc gcagcaggga ggcaaacaat gaatcaacaa ctctcctggc gcaccatcgt      4920
cggctacagc ctcgggaatt gctaccgagc tcgaatttcc ccgatcgttc aaacatttgg      4980
caataaagtt tcttaagatt gaatcctgtt gccggtcttg cgatgattat catataattt      5040
ctgttgaatt acgttaagca tgtaataatt aacatgtaat gcatgacgtt atttatgaga      5100
tgggttttta tgattagagt cccgcaatta tacatttaat acgcgataga aaacaaaata      5160
tagcgcgcaa actaggataa attatcgcgc gcggtgtcat ctatgttact agatcgggaa      5220
ttgatccccg ggtacc                                                     5236
```

<210> SEQ ID NO 3  
<211> LENGTH: 21  
<212> TYPE: DNA  
<213> ORGANISM: Artificial  
<220> FEATURE:  
<223> OTHER INFORMATION: Primer

<400> SEQUENCE: 3

```
gcttggtctt acttcatcgt c                                                  21
```

<210> SEQ ID NO 4  
<211> LENGTH: 27  
<212> TYPE: DNA  
<213> ORGANISM: Artificial -continued

```
<220> FEATURE:
<223> OTHER INFORMATION: Primer

<400> SEQUENCE: 4
ccggatcctc caccacgtag acgaagg                                           27
```